(12) United States Patent
Okuno et al.

(10) Patent No.: US 6,629,060 B2
(45) Date of Patent: Sep. 30, 2003

(54) SUPPORT METHOD, QUALITY CONTROL METHOD, AND DEVICE THEREFOR

(75) Inventors: Ken'ichi Okuno, Kakogawa (JP); Hiroyuki Morihara, Kobe (JP); Tadayuki Yamaguchi, Kobe (JP); Tomomi Sugiyama, Kobe (JP)

(73) Assignee: Sysmex Corporation, Hyogo (JP)

( * ) Notice: Subject to any disclaimer, the term of this patent is extended or adjusted under 35 U.S.C. 154(b) by 103 days.

(21) Appl. No.: 09/725,498

(22) Filed: Nov. 30, 2000

(65) Prior Publication Data

US 2002/0128801 A1 Sep. 12, 2002

(30) Foreign Application Priority Data

Nov. 30, 1999 (JP) .......................... 11-341085

(51) Int. Cl.$^7$ .............................. G06F 15/00
(52) U.S. Cl. ................ 702/187; 702/19; 702/81; 702/84; 702/187; 422/3; 422/50; 422/62; 422/99; 436/8; 436/50; 340/500; 340/514; 340/523; 709/205; 709/213; 709/310
(58) Field of Search ................ 702/19, 21, 25, 702/27, 29–32, 50, 55, 81–84, 100, 108, 122, 179, 188, 180, 183, 186; 422/3, 50, 62, 67, 68.1, 93, 98, 99, 105, 108, 116, 119; 707/10, 101, 102, 200, 201, 204, 205; 709/100, 102–104, 106, 107, 201–203, 205–207, 213–219, 223–229, 310; 340/500–501, 514–517, 520, 523, 540, 603, 632, 633, 691.1, 825, 286.01, 815.58

(56) References Cited

U.S. PATENT DOCUMENTS 5,366,896 A * 11/1994 Margrey et al. .............. 436/48

FOREIGN PATENT DOCUMENTS

EP 0893772 1/1999

OTHER PUBLICATIONS

Korper et al., 'Enzyme Immune Assay–Portable Microcomputer Interfaced System', Dec. 1983, vol. 7, IEEE, pp. 248–249.*

* cited by examiner

*Primary Examiner*—Marc S. Hoff
*Assistant Examiner*—Elias Desta
(74) *Attorney, Agent, or Firm*—Shinjyu Global IP Counselors, LLP

(57) ABSTRACT

The present invention quickly resolves troubles in an analyzer and performs effective external quality control management. An analyzer (2) and a control device (1) are connected by a network (3). Error data and sample data taken from assay of a quality control substance are transmitted from the control device (1) to the analyzer (2). The analyzer (2) is made to be remotely operable from the control device (1) and when troubles arise repair from the control device (1) is possible. The control device (1) tallies sample data, and provides the tally results to a Web page. The analyzer (2) accesses the Web page using a WWW browser, and can perform external quality control in real time.

28 Claims, 22 Drawing Sheets

| Machine Information | | | | | | |
|---|---|---|---|---|---|---|

Facility Name

Type of Machine          Serial No.

| Error Log | Program Log | Settings | Operation Count |
|---|---|---|---|

| Date | Time | Text Message | Error Code | Detailed Code 1 | Detailed Code 2 |
|---|---|---|---|---|---|
| 1999/7/21 | 13:13 | Short sample | 161010 | | |
| 1999/7/21 | 13:13 | Short sample | 161010 | | |
| 1999/7/16 | 12:01 | Blood cannot be siphoned | 161010 | | |
| 1999/7/15 | 14:52 | HGB Error | 415000 | 2210 | 6085 |
| 1999/7/15 | 14:52 | <Assay Error> | 417010 | | |
| 1999/7/15 | 11:27 | Blood cannot be siphoned | 161000 | | |
| 1999/7/14 | 14:42 | Please change the SNR | 133160 | | |
| 1999/7/14 | 14:41 | Short sample | 161010 | | |
| 1999/7/14 | 12:56 | Short sample | 161010 | | |
| 1999/7/13 | 9:56 | FCM sheath liquid cannot be siphoned | 132019 | | |
| 1999/7/12 | 9:21 | Please change the RED | 132019 | | |
| 1999/7/9 | 15:28 | Abnormality in RET computation sampling | 413090 | | |
| 1999/7/9 | 11:38 | 0.3 kg/cm2 pressure abnormality | 111030 | 325 | |
| 1999/7/9 | 11:38 | 0.3 kg/cm2 pressure abnormality | 111030 | 25 | |
| 1999/7/9 | 11:38 | 0.3 kg/cm2 pressure abnormality | 111030 | 150 | |
| 1999/7/8 | 14:09 | Please change the EPK | 131029 | | |
| 1999/7/8 | 13:06 | 0.3 kg/cm2 pressure abnormality | 111030 | 265 | |
| 1999/7/8 | 12:58 | <Assay Error> | 417010 | | |
| 1999/7/8 | 12:57 | 0.3 kg/cm2 pressure abnormality | 111030 | 320 | |
| 1999/7/8 | 11:56 | HGB blank liquid discharge error | 415010 | 1175 | 1194 |
| 1999/7/8 | 11:56 | HGB error | 415000 | 1194 | 539 |
| 1999/7/8 | 11:56 | HGB error | 415000 | 880 | 749 |

*Fig. 8*

| Date | Time | Text Message | Error Code | Detailed Code 1 | Detailed Code 2 |
|---|---|---|---|---|---|
| 1999/7/13 | 9:56 | FCM sheath liquid cannot be siphoned | 132019 | | |
| 1999/7/12 | 9:21 | Please change the RED | 132019 | | |
| 1999/7/9 | 15:28 | Abnormality in RET computation sampling | 413090 | | |
| 1999/7/9 | 11:38 | 0.3 kg/cm2 pressure abnormality | 111030 | 325 | |
| 1999/7/9 | 11:38 | 0.3 kg/cm2 pressure abnormality | 111030 | 25 | |
| 1999/7/9 | 11:38 | 0.3 kg/cm2 pressure abnormality | 111030 | 150 | |
| 1999/7/8 | 14:09 | Please change the EPK | 131029 | | |

} Record of Abnormalities Determined

Fig. 9

| Date | Time | Program Name | Version |
|---|---|---|---|
| 1999/7/21 | 13:13 | ANALYZE | 00-08 |
| 1999/7/21 | 13:13 | LOADER (ROM4XE21) | 00-01 |
| 1999/7/21 | 13:13 | TEMP. (ROM2XE21) | 00-02 |
| 1999/7/21 | 13:13 | SAMPLER (ROM3XE21) | 00-04 |
| 1999/7/21 | 13:13 | CPU | 00-09 |
| 1999/7/21 | 13:13 | SEQ | 00-08 |
| 1999/7/21 | 13:13 | IPU ( J ) | 00-10 |

| Date | Time | Main Unit | Piercer | SRV | Shutdown | FFS | FCM Motor |
|---|---|---|---|---|---|---|---|
| 1999/7/21 | 13:13 | 956842 | 15278 | 2584 | 58794 | 6574 | 78924 |
| 1999/7/19 | 13:13 | 956500 | 14936 | 2242 | 58452 | 6232 | 78582 |
| 1999/7/16 | 13:13 | 956158 | 14594 | 1900 | 58110 | 5890 | 78240 |
| 1999/7/15 | 13:13 | 955816 | 14252 | 1558 | 57768 | 5548 | 77898 |
| 1999/7/14 | 13:13 | 955474 | 13910 | 1216 | 57426 | 5206 | 77556 |
| 1999/7/13 | 13:13 | 955132 | 13568 | 874 | 57084 | 4864 | 77214 |
| 1999/7/12 | 13:13 | 954790 | 13226 | 532 | 56742 | 4522 | 76872 |

Error Determination Patterns

| Pattern | Determination Method | Range, Unit |
|---|---|---|
| 1 | Determine by count of errors ocurring in 1 day.<br>Example: 1 or more errors occurring in 1 day. | 1 to 20 times (per time) |
| 2 | Determine by count of errors ocurring within a timeframe.<br>Example: Same error occuring twice within 1 hour. | 1 to 12 Hours (per hour) |
| 3 | Determine by number of consecutive days error has Occurred. *1<br>Example: Error occurring 2 consecutive days. | 1 to 5 days (per day) |
| 4 | Do not determine | |

*Fig. 12*

| Specified Level | Parameters | Pattern |
|---|---|---|
| Level 1 | One or more errors occurring in 1 day. | 1 |
| Level 2 | Same error occurring 3 or more times in 1 day. | 1 |
| Level 3 | Same error occurring 10 or more times in 1 day. | 1 |
| Level 4 | Do not determine | 4 |

*Fig. 13*

| Lot No. | Quality Control Substance Type | Measurement Mode | Device ID | Time Zone | Time of Day | Sample Data |
|---|---|---|---|---|---|---|

*Fig. 19*

When the Past 24 Hours are Subject to Analysis

When the Past 48 Hours are Subject to Analysis

Conceptual Diagram of Today's Analysis Processing

Conceptual Diagram of the Previous Day's Analysis Processing

SUPPORT METHOD, QUALITY CONTROL METHOD, AND DEVICE THEREFOR

BACKGROUND OF THE INVENTION

1. Technical Field

The present invention relates to quality control in, and technology for facilitating support of analyzers.

2. Description of Related Art

Blood tests and other forms of clinical examination require that samples such as blood and urine be analyzed for a variety of test items. Analyzers that employ assaying methods suited to the characteristics of the analysis items perform sample assays. Analyzers have sophisticated mechanisms that allow them to assay, with a high degree of sensitivity, extremely low concentrations of a substance, and to assay trace amounts of sample for ten or more items. To maintain the accuracy of the test results, operations in each of the mechanisms are monitored.

When problems arise in operation of the mechanisms, the analyzer issues a warning to that effect, alerting the user to the problem in the analyzer. In such cases, a user will deal with the problem by following the operating manual or, for example, by calling a support center, explaining the circumstances, and following the instructions of the technician. When the user cannot take care of it single-handedly, the support center dispatches a technician to do so.

Nevertheless, in clinical testing, merely monitoring the analyzer mechanisms is insufficient for governing test results on vital components with satisfactory accuracy. Quality control is therefore performed. Samples identical with the vital components, or samples that are their analogues, are assayed as quality control substances, and the assay results are monitored.

Both internal and external methods are utilized for quality control. Internal quality control is a method of assaying identical quality control substances daily with the same analyzer, and monitoring whether stable assay results are being obtained. External quality control is a method of monitoring whether assay results are being obtained that are the same as results assayed by an identical analyzer employed outside those facilities.

In order to carry out external quality control, however, the same quality control substance has to be sent from a statistical tallying center to each facility; the quality control substance has to be assayed at each facility; those assay results ("sample data" hereinafter) have to be sent from each facility to the statistics center; and the sample data has to be tallied by the statistics center. This means that the facilities first learn of the external quality control results when the tally is sent back from the statistics center. From the time the quality control substance is sent out until the time the tally is returned routinely takes one to two months. Sometimes it is necessary to wait until the statistics center accumulates a set number of sample data returns.

A first issue the invention addresses relates to measures taken when trouble has arisen. Because the today's analyzers are operated under the control of sophisticated programs, instances in which a user is unable to cope with the problem single-handedly are increasing. When such is the case, the user has to wait until a technician identifies the problem.

The only option is to wait for the technician's visit if a systematic problem can only be resolved by changing out or adjusting an analyzer component. Nevertheless, these are not the only reasons users cannot cope with breakdowns single-handedly. There appear to be many cases in which users ought to be able to resolve the trouble on their own. In some instances, the trouble in the analyzer is not resolved because the user cannot adequately explain the status of the problem; in others, the user cannot properly carry out the analyzer operations necessary to resolve the trouble.

Because assay is not possible while an analyzer is down, patient test results in clinical examination cannot be reported to the diagnosing physician. For samples like blood with low preservation stability, assaying the following day would mean lower accuracy test results, and therefore blood has to be drawn from the patient again.

A second issue the invention addresses is that with external quality control, as described above, confirmation is only by waiting for the tally from the statistics center. This normally is done once a year, and at most on the order of only three or four times a year.

To raise the reliability of assay data per se, quality control by definition should be carried out and the results checked before each day's sample assays. In other words, if the quality control sample data falls outside a predetermined range, this can mean that something has gone wrong and that the analyzer is not in sufficient working order. Sample assay should be carried out following adjustment of the analyzer to bring the data within the predetermined range. With current external quality control, however, the tally results come back one or two months after assay, and are used for no more than confirming after-the-fact the status of the device at the time assay was made.

Wherein a substance such as blood that is liable to transform (denature) over time is the assay subject, the freshness of the quality control substance employed in the sample data assay must be at the same level among each of the facilities taking part in external quality control. When quality control substances are sent out to facilities to collect sample data, inevitably the assaying days have a propensity to be diverse. Herein, because the freshness of the quality control substances that are the basis for the sample data collected tends to vary, the reliability of the tally results is diminished.

SUMMARY OF THE INVENTION

It is an object of the present invention to enable rapid, exact resolution of analyzer problems and effective external quality control.

To address the foregoing first issue, an aspect of the present invention presents a support method employed in an information terminal connected to analyzers via a network, the support method comprising: collecting from the analyzers via the network predetermined log information indicating the operational history of the analyzers; storing the collected log information for each analyzer; and outputting the collected log information in response to instruction by the operator of the information terminal.

Communication between the information terminal and the analyzers is performed through a dedicated telephone line (in Japan, for example, an NTT line), the Internet or the like. The operational history of each analyzer can be seen by support personnel at, for example, a support center, and this can prevent analyzers from being down and can facilitate repair work. Collecting log information by SMTP (Simple Mail Transfer Protocol) has the advantage of allowing for easy expansion of the system over a network, since SMTP is usually not subject to the restrictions of firewalls and the like.

In this information-terminal employed support method, it is preferable to operate the analyzer from the information terminal via a network.

Support personnel can operate the analyzer while looking at the analyzer operational history stored on the information terminal. When an analyzer is down, remote support personnel can quickly resolve the trouble without having to travel to the actual site, leading to a significant reduction in down time.

Furthermore, good use can be made of a user support method wherein error determination parameters are prepared in advance; predetermined error information is extracted from the log information; error histories are created by consulting (looking up) the error determination parameters; and error histories and the analyzer are correlatively stored.

For example, error level is determined based upon how many times the same occurrence occurred in one day. Along with error type, error message, date and time, and other error log information, error levels are correlated with analyzers and used in forecasting and solving trouble.

Further to address the first issue noted above, another aspect of the present invention presents a support method employed in an analyzer connected to a predetermined information terminal via a network, wherein predetermined log information showing the operational history of the analyzer is transmitted at a predetermined timing to the information terminal via the network.

For example, in the shutdown process for an analyzer the operational history for that day is sent to the information terminal. The predetermined information terminal performs the same function as the information terminal in the above first aspect of the invention.

In the above support method used in an analyzer, it is preferable to accept operations from a dedicated information terminal via the network.

Accepting control operations from an information terminal though the information terminal is in a distant support center allows for the fast resolution of troubles.

To address the foregoing second issue, another aspect of the present invention presents a quality control method employed in an information terminal connected to analyzers via a network, wherein:

A: sample data on assays made by the analyzers on predetermined quality control substances is received via a network;

B: the received sample data is stored;

C: the stored sample data is tallied for each analyzer and each quality control substance; and D: the tally results for the received sample data are provided to the analyzers within a predetermined timeframe.

Communication between the information terminal and the analyzers is performed through a dedicated NTT line, the Internet or the like. The analyzers perform daily assay of quality control substances, such as control blood, and transmit the assay data to the information terminal. The information terminal stores the assay data sent from analyzers and tallies the stored assay data for each analyzer and each quality control substance. Each time the information terminal receives sample data from an analyzer it performs a new tally (statistical calculation).

In order that the tally results be on parameters in which the freshness of the quality control substances is alike, the statistical calculations (tallying) may be on sample data assayed within a predetermined timeframe, for example, within twenty-four hours of being received. When an analyzer requests tally results, the latest tally results at that point are provided in real time. In the present invention communications by SMTP, which is unlikely to be subject to the restrictions of firewalls, are preferable.

To address the foregoing second issue, another aspect of the present invention presents a quality control method employed in analyzers connected to a dedicated information terminal via a network, wherein:

A: sample data on assays made by the analyzers on predetermined quality control substances is transmitted to the information terminal via the network;

B: tally results on the sample data are requested of the information terminal;

C: the tally results on sample data the information terminal has collected from the analyzers within a predetermined timeframe are acquired from the information terminal; and D: the tally results are output.

Utilizing this method, the results that the information terminal in the above information-terminal employed quality control method as tallied are output to an analyzer display, printer or other output device. A user consults the output results to make an analyzer quality control check on his or her own.

Another aspect of the present invention also presents a computer-readable storage medium on which is recorded a program for executing the foregoing support method employed in an information terminal or analyzer. Conceivable recording media include floppy disks, hard drives, semiconductor memory, CD-ROMs, DVDS, and MO disks.

Another aspect of the present invention also presents a control device connected to analyzers via a network, comprising: reception means for receiving from the analyzers via the network predetermined log information indicating the operational history of the analyzers; storage means for storing log information for each analyzer; and output means for outputting log information in response to instruction by an operator.

This has the same operational effect as the above support method used in an information terminal.

Another aspect of the present invention presents an analyzer connected to a dedicated information terminal via a network, comprising transmission means for transmitting predetermined log information showing operational history of the analyzer at a predetermined timing to the information terminal via the network.

This has the same operational effect as the above support method used in an analyzer.

Another aspect of the present invention also presents a control device connected to analyzers via a network, comprising: reception means for receiving via the network sample data on assays made by the analyzers on predetermined quality control substances; storage means for storing received sample data; statistical tallying means for tallying the stored sample data for each analyzer and each quality control substance; and provision means for providing the tally results for the received sample data to the analyzers within a predetermined timeframe.

This has the same operational effect as the above support method used in an information terminal.

Another aspect of the present invention also presents an analyzer connected to a dedicated information terminal via a network, comprising: transmission means for transmitting to the information terminal via the network sample data on assays made by the analyzers on predetermined quality control substances; request means for requesting of the information terminal tally results on the sample data; acquisition means for acquiring from the information terminal the tally results on sample data the information terminal has collected from the analyzers within a predetermined timeframe; and output means for outputting the acquired tally results.

This has the same operational effect as the above support method used in an analyzer.

BRIEF DESCRIPTION OF THE DRAWINGS

FIG. 8 is an example of an error information selection screen;

FIG. 9 is an error log display example;

FIG. 12 is an example of error determination patterns;

FIG. 13 is an example of an error determination table;

FIG. 19 is a conceptual configurational diagram of data sent from an analyzer to a control device;

DETAILED DESCRIPTION OF THE PREFERRED EMBODIMENTS

The support method and quality control method of the present invention will be explained in detail with reference to the figures.

First Embodiment

Overview

This embodiment will be explained using as an example a remote support system that is a realization of the methods of the present invention. This remote support system is constituted by an analyzer owned by a laboratory (i.e., a user) and a control device of the party providing the system, the devices being interconnected by a dedicated network.

The analyzer transmits predetermined log information according to a predetermined timing to the control device over the network. Contained in the log information are operational information showing the operational conditions of the analyzer and sample data. The operational information comprises error information, number of times operated, operation program, set-up parameters and the like for each analyzer. The sample data is assay data from a quality control substance.

The control device performs a support process, collecting log information from each analyzer, editing the log information for each analyzer according to content, and storing the information, and performs a Quality control (QC) process.

A. Support Process

The control device edits operational information from collected log information and stores that information. The control device also analyzes error content based on operational information, and if there is a significant error it displays that error. Because a technician can review at the control device the log information of the analyzer where the error arose, he can sufficiently understand the conditions of the machine without needing a detailed explanation from the user, and can work on finding the cause of the trouble.

In addition, the analyzer is provided with the capability to remotely operate the analyzer. Therefore, a technician does not actually have to go to the laboratory, but can work on the analyzer directly from the control device. Furthermore, the control device can analyze error information, predict when an analyzer will have trouble, and take measures to prevent trouble before it occurs.

B. QC Process

A control device 1 tallies, i.e., makes statistical computations on, sample data from a quality control substance assayed at each analyzer 2 per type of analyzer 2 and per type of quality control substance. Each time the control device 1 receives sample data, it updates the tally results for the same type of sample data at the same type of machines, and provides the latest tally results on a Web page. By accessing this Web page, the analyzer 2 can acquire the latest tally results. When an analyzer attempts to access the Web page, the control device authenticates the authentication information input by the analyzer. In this manner, soon after assaying a quality control substance, a user can confirm in real time the very latest tally results for the quality control substance.

Configuration (1) Overall Configuration

Figure 1:
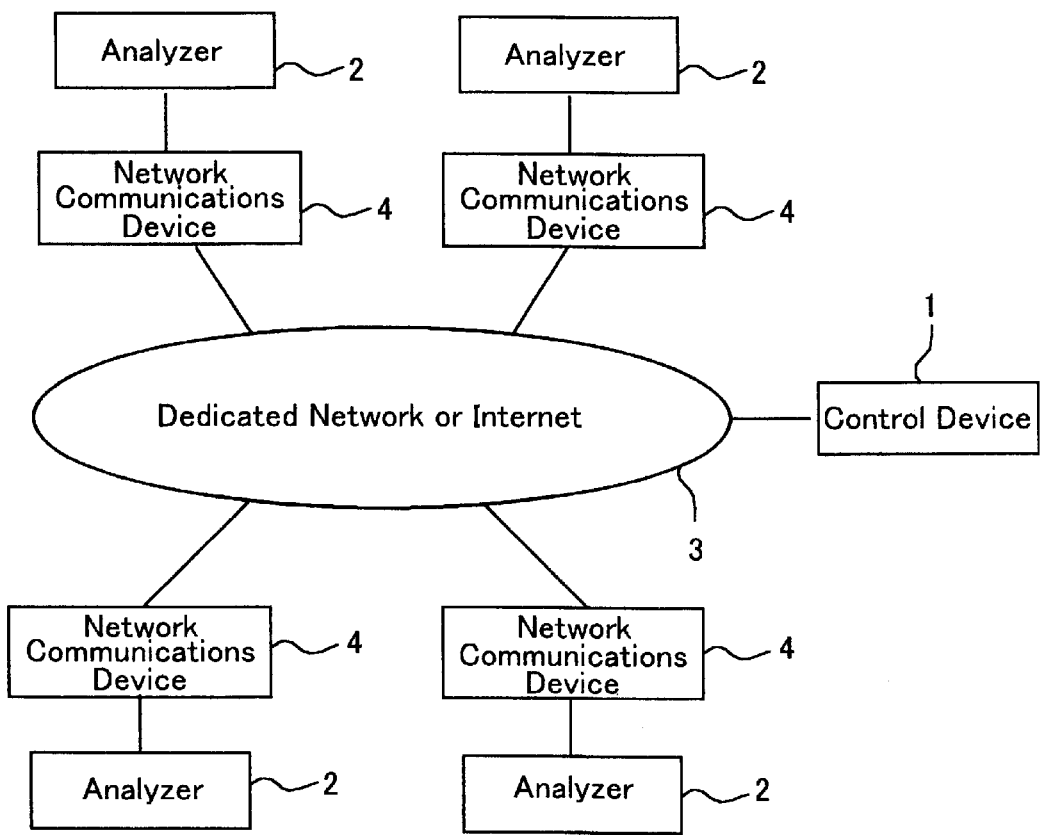
FIG. 1 is an overall configurational diagram of a remote support system in one example relating to the first embodiment.

FIG. 1 is one example of an overall block diagram of a remote support system according to the first embodiment. In the remote support system according to this embodiment, the control device 1 and the analyzers 2 are interconnected over a dedicated network 3. .

The analyzer 2 is interconnected with the dedicated network 3 via a network communications interface 4. Possible analyzers include hemanalysis and urinalysis devices. Personal computers, workstations and the like can be used as the control device 1. Dial-up routers and modems can be used as the network communications interface 4.

One example that could be given of a dedicated network 3 would be a dedicated telephone line that the provider of this system is able to use exclusively, through a contract with the company providing the telephone line. Other types of networks than dedicated networks can be used, such as the Internet and intranets and LANS.

(2) Control Device

Figure 2:
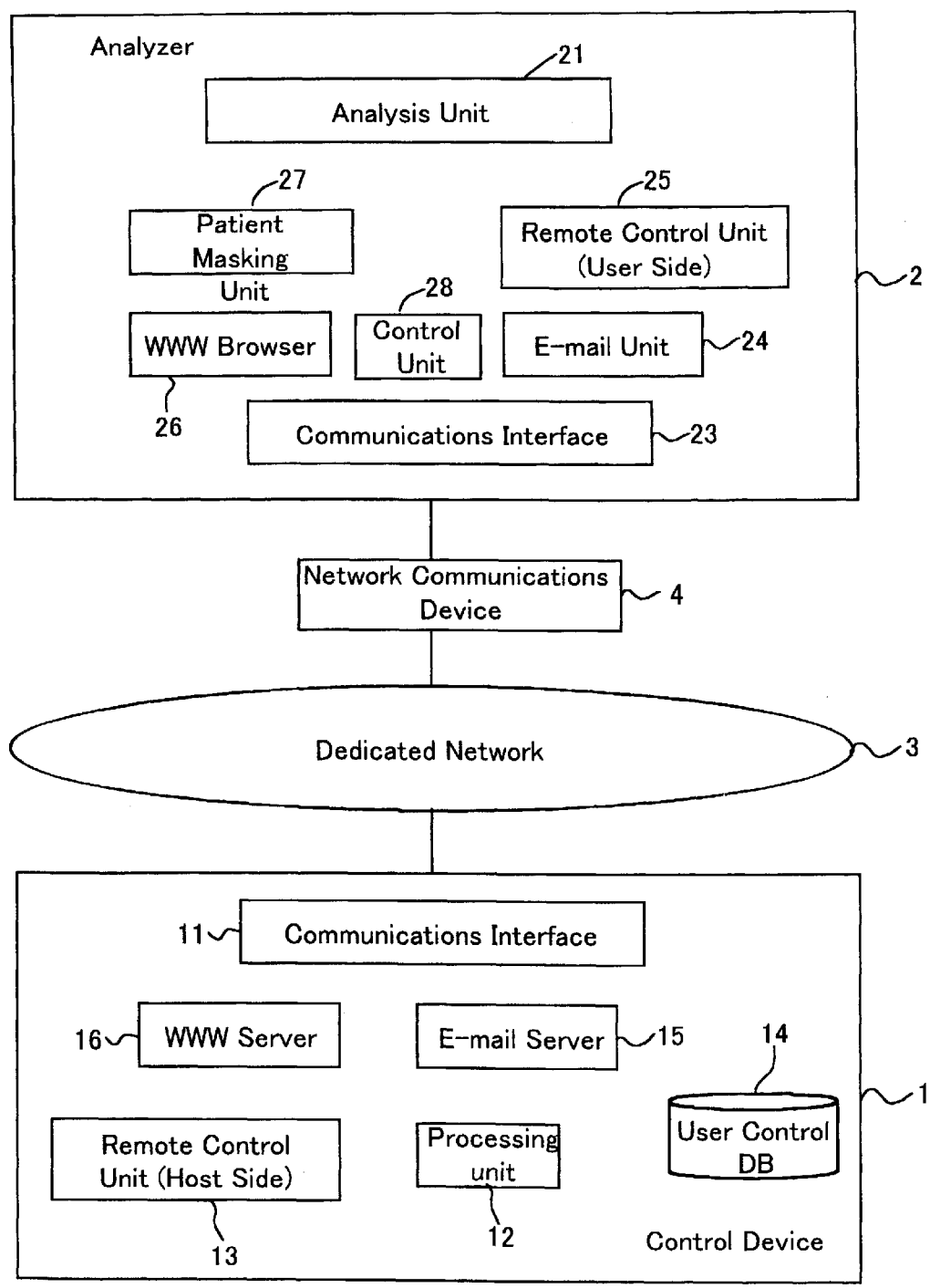
FIG. 2 is a block diagram indicating functional configuration.

FIG. 2 is a block diagram showing the functions and constitution of the control device and the analyzer.

The control device comprises a communications interface 11, a processing unit 12, a user control database (an example of memory means) 14, an e-mail server 15, a WWW server 16 and a host side remote control unit (an example of remote control means) 13.

The communications interface 11 establishes a connection with analyzers.

Figure 14:
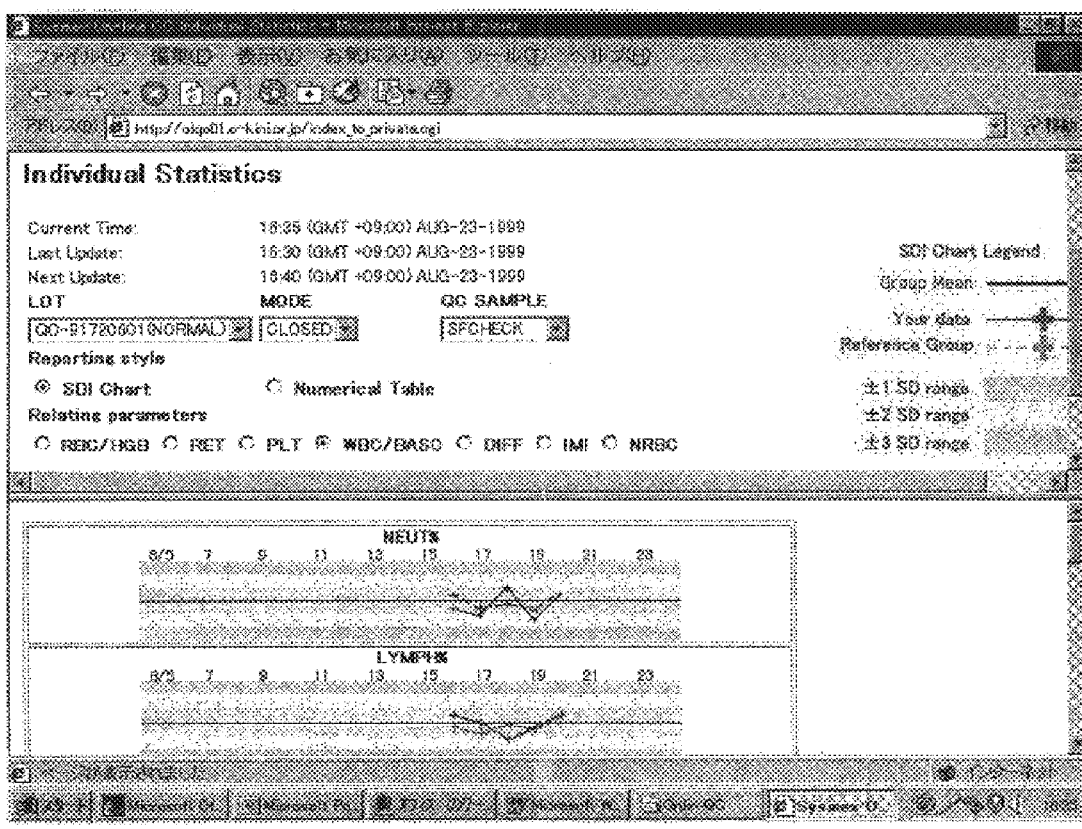
FIG. 14 is a Web page display example (menu screen) created by a QC process.
Figure 15:
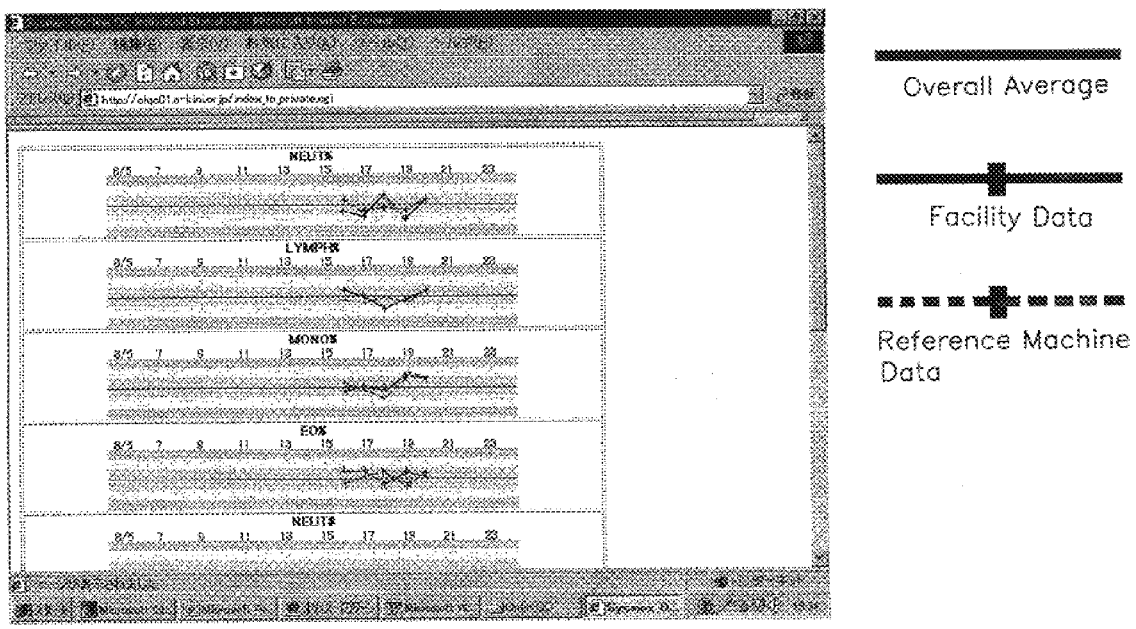
FIGS. 15 and 16 are Web page display examples (tally results) created by the QC process.

The processing unit 12 performs support process and QC process, using the user control database 14. The support process displays predetermined error log at the control device, making it possible to find the cause of the trouble. FIGS. 8 through 11 show display examples of the error log output by the processing unit 12. The QC process makes possible real time external quality control at the analyzer. FIGS. 14 and 15 show examples of Web pages for tally results created by the QC process. These examples will be discussed in detail below.

The user control database 14 stores at each analyzer error log, number of times operated, QC data, log information and the like.

The e-mail server 15 receives log infonnation and sample data from analyzers through SMTP. This way, the mail server 15 functions as collection means in this embodiment. The communications protocol is not limited herein to SMTP, but SMTP has the advantage of facilitating future expansion of this system, due to the fact that it is usually not subject to the restrictions of firewalls and the like.

The WWW server 16 provides a WWW browser on the analyzer with the web pages that processing unit 12 has created. This way, the WWW server 16 functions as output means in this embodiment.

The remote control unit (host end) 13, by being linked with the remote control unit (user end) on the analyzer 2, makes possible the remote operation of the analyzer 2. Because the two units are inter-linked, the analyzer can be logged onto remotely, the window displayed at the analyzer is displayed at the remote control unit (host end) 13, and the analyzer can be operated pursuant to the operations input from the remote control unit (host end) 13.

(3) Analyzer

An analyzer 2 has an analysis unit (an example of assay means) 21, a communications interface 23, an e-mail server 24, a user side remote control unit (an example of remote control means) 25, a WWW browser 26, a patient masking unit 27 and a control unit 28.

The analysis unit 21 assays the quality control substances and generates sample data.

The communications interface 23, as with the communications interface 11 in the above control device 1, establishes a connection.

The e-mail server 24 sends log information showing the operational history of an analysis unit 21 and sample data to the control device using SMTP. This way, the mail server 24 functions as transmission means in this embodiment.

The remote control unit (user end) 25, by being inter-linked with the remote control unit (host end) 13, makes possible the operation of the analyzer 2 from the control device 1.

The WWW browser 26 acquires Web pages from the control device based on instructions from a user. This way, the WWW browser 26 functions as retrieval means.

The patient masking unit 27 ensures that when the analyzer 2 is operated from the control device 1, patient information is not displayed at the control device.

The control unit 28 functions as operational information generation means, classifying means and determination means, and controls the operations of the analysis unit 21 and of the other constituent elements of the analyzer 2.

Process Flow

An explanation will be given of the process performed by the control device and analyzer in a remote support system.

(1) Overall System Process Flow

Figure 3:
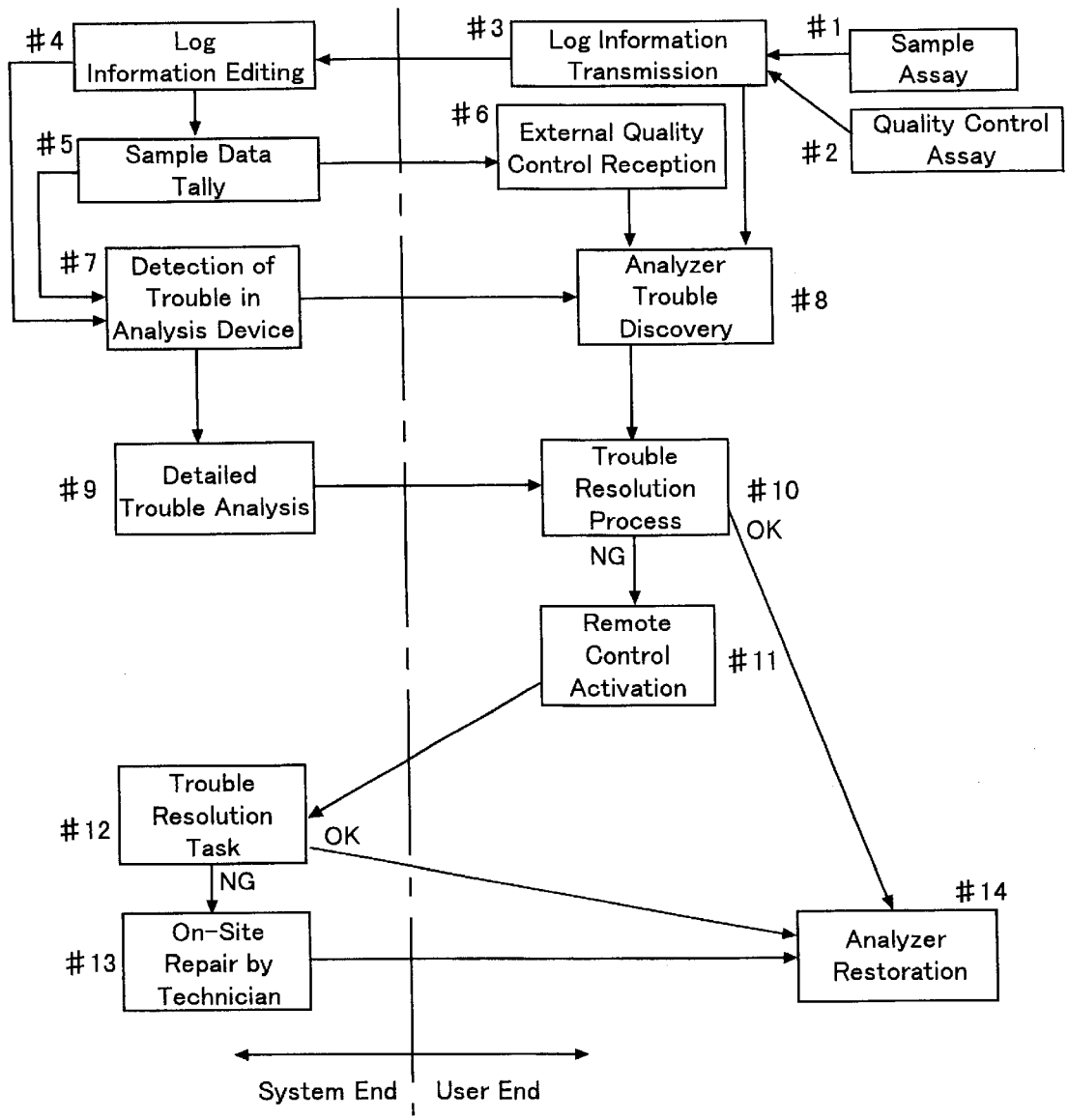
FIG. 3 is one example of process flow in the remote support system.

An explanation will be made in detail of the process flow of the overall system. FIG. 3 is an explanatory diagram showing an example of the flow of user support in a remote support system.

The analyzer 2 performs standard sample measurement (#1), and its operational information is transmitted to the control device 1 according to a predetermined timing (#3). The transmission is made in real time if the operational information contains error information or other urgent information (example of first operational information). The transmission is made when the analyzer is shutdown if the operational information is not urgent, such as number of times operated and sample measurement results (examples of second operational information). Error information is also displayed at the analyzer 2, too, and the user discovers that there is trouble at the analyzer 2 (#8).

The control device 1 classifies operational information sent from the analyzer 2 according to type and stores this in the user database 14 (#4). When there is major error information in the stored operational information, or when there are other indications that a predetermined major error will occur, such as when there is minor error information, but the error occurs frequently or when error conditions are worsening, the trouble the analyzer is having is detected based on certain settings (#7).

When the analyzer 2 assays a quality control substance, unlike routine sample assay results, the sample data is transmitted to the control device 1 in real time (#3). The analyzer 2 reads a barcode affixed to the assay sample container, determines whether that sample is a quality control substance or not, and based on that determination, transmits the sample data. The control device 1 takes the new sample data and updates the tally results (#5).

The user, after sample data assay, acquires the tally results that the control device 1 has tallied (#6) and confirms the external accuracy. The control device 1 updates the Web pages in accordance with updates to the tallied data. The analyzer 2 accesses a Web page, and when access is authenticated, the latest tally results and the sample data are provided on the Web page.

In this manner, a user can quickly confirm not just internal quality control results, but external quality control results as well, and can discover malfunctions in an analyzer in real time (#8).

The control device 1 tallies quality control data. If the quality control results fall outside of a predetermined range, or if a worsening of the quality control data is anticipated, trouble in the analyzer 2 is detected based on predetermined settings (#7). For example, data is trending away from median values. If trouble at the analyzer 2 is detected at the control device 1, the user is notified to that effect (#8).

If trouble at the analyzer is discovered (#8), the user carries out processes to resolve the trouble (#10). The control device 1 analyzes the trouble from the edited operational information of that analyzer 2 (#9), and provides the user with the most suitable information for solving the trouble.

If it is difficult for the user to resolve the trouble himself, the user activates the remote control unit of the analyzer (#11). A technician at the support center remotely operates the analyzer 2 and performs task for resolution of the trouble via the remote control unit of the control device (#12). Thereupon the screen of the analyzer and the screen of the control device are linked. In this manner, with regard to troubles that can be resolved through operation of the analyzer, even a complicated problem can be resolved through remote operation from the support center (#14). For troubles that cannot be resolved thus, a technician would go and make repairs (#13, #14).

(2) Control Device Process Flow

Next, the flow of a process that the control device 1 performs in a remote support system will be explained in detail.

(2-1) Collection Process

Figure 4:
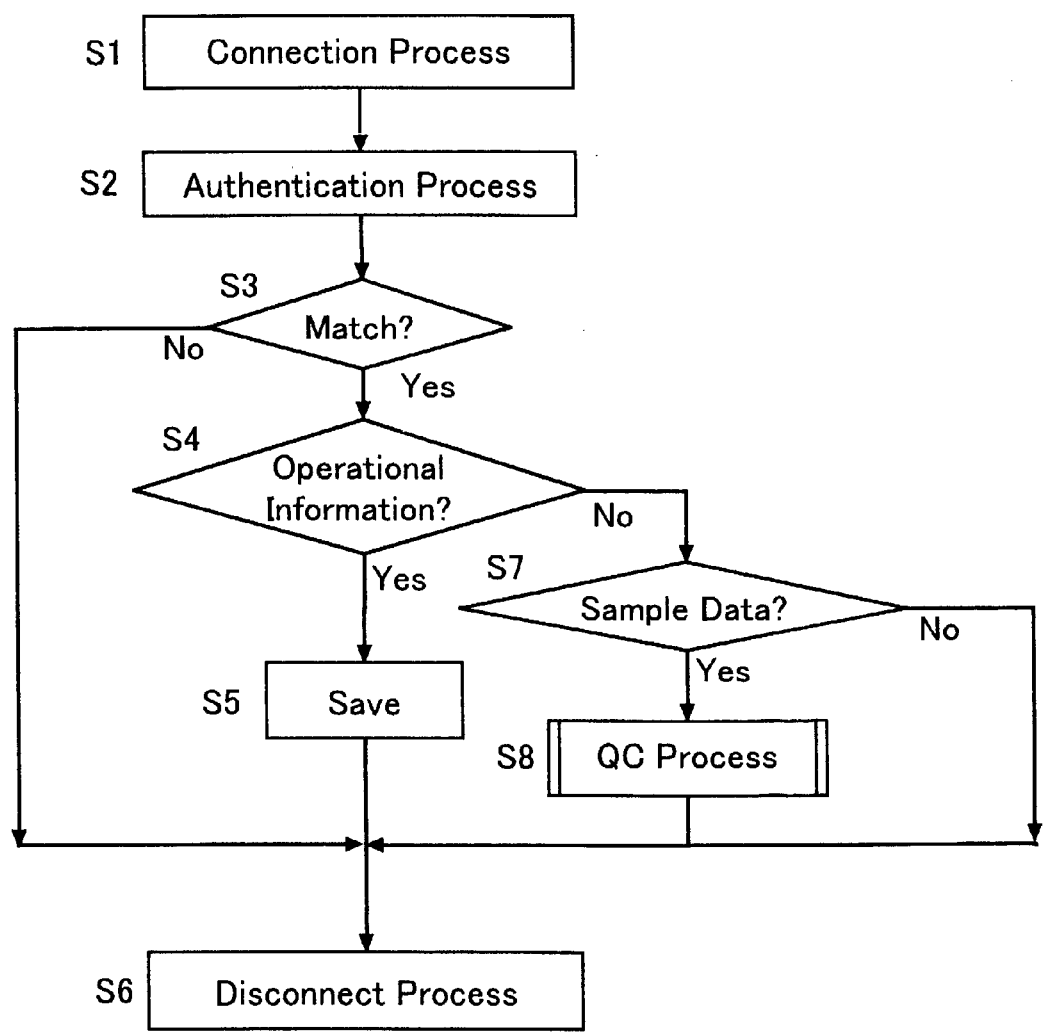
FIG. 4 is a flowchart showing one example of flow in a main process performed by a control device.

FIG. 4 is a flowchart showing one example of the flow of the main process that the control device 1 performs. In the main process, the control device 1 collects log information from the analyzer 2, and if it is operational history, stores it, and if it is sample data, performs QC process. The following process commences by means of the dial-up router from the analyzer 2.

In Step S1, the communications interface 11 performs a connection process to establish a connection with the analyzer 2.

In Step S2, the processing unit 12 performs a prescribed authentication process. In other words, it determines whether the authentication information sent from the analyzer 2 matches the user information in the user database.

In Step S3, the processing unit 12 performs a process according to the authentication results. If the determination is that the authentication information matches, operation proceeds to Step S4. If it doesn't match, then the connection is cut or another like process is performed.

In Step S4, the e-mail server 15 receives data from the analyzer 2. The processing unit 12 determines whether the received data is predetermined operational information or not. Operational information is predetermined information other than sample data, for example, error data, number of times operated, program log, and set-up information. If the answer is "yes," then Step S5 ensues; if "no," Step S6 ensues.

In Step S5, the processing unit 12 temporarily saves the received operational information. This is for use in the support process, which is discussed below. In the support process, for example, operational information from each analyzer 2 until 00:00 midnight, when the date changes, is stored; when the time reaches 00:00, operational history is created based on the operational information received that day.

In Step S6, communications interface 11 severs the connection with the analyzer 2.

In Step S7, the processing unit 12 determines whether the received data is sample data from assay of a quality control substance. If the determination is "yes," then Step S8 ensues, proceeding to the QC process, which is discussed below. In other words, sample data, including received data, is tallied, and the Web page for each analyzer is updated. If the answer is "no," the above-described Step S6 ensues, and the connection is severed.

(2-2) Support Process

Figure 5:
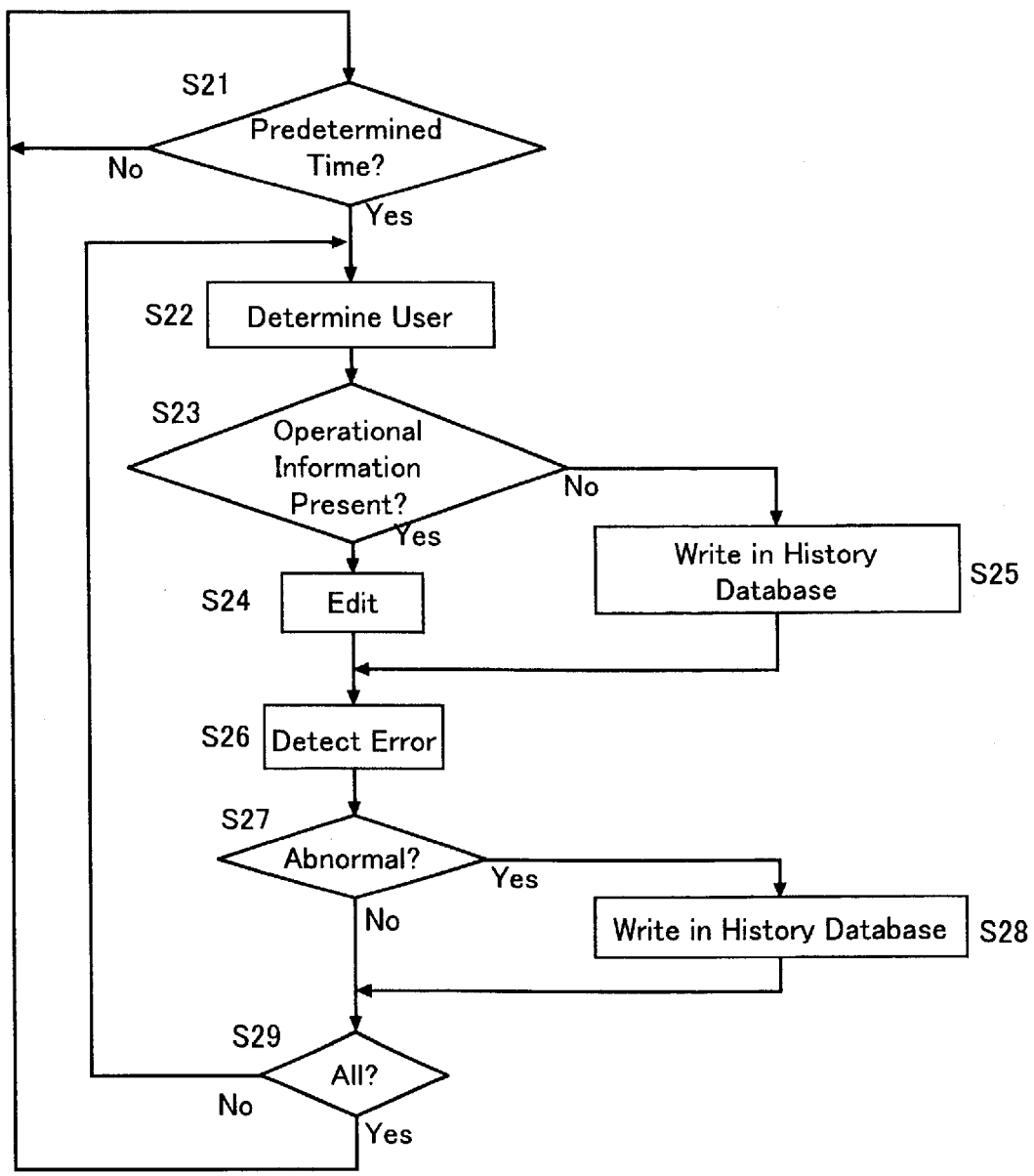
FIG. 5 is a flowchart showing one example of support process flow performed by the control device.

FIG. 5 is a flowchart showing one example of flow in a support process that the control device 1 performs independently of the main process. Every time the date changes, the control device 1 edits the operational information received that day and writes that to the history database.

In Step S21, the processing unit 12 is waiting for a predetermined time, for example, 00:00.

In Step S22, the processing unit 12 determines which analyzer 2 among those registered in the user control database 14 is the subject user.

In Step S23, the processing unit 12 determines whether it has received operational information showing operating conditions for that date for the subject user. If the determination is "yes," Step S24 ensues. If the determination is "no," then Step S25 ensues.

In Step S24, the processing unit 12 edits operational information for each analyzer and each subject matter, and writes this to the history database. For example, it edits error information, number of times operated, operation program, and setting parameters, in separate table format with date and time, and writes this to the history database.

In Step S25, the processing unit 12 writes to the user control database 14 predetermined error information showing that operational information could not be acquired. Possible examples of error information include analyzer name, date, time, error number showing the error that arose, and error message corresponding to error number.

In step S26, the processing unit 12 searches for a predetermined error based on the error information of the subject user. For example, using the methods for determination shown in FIG. 12, error levels are decided, as in the example shown in FIG. 13, from error type and the frequency with which the same type of error occurs.

In Step S27, the processing unit 12 uses the search results to determine whether or not errors are contained in the operational information of the subject user. Unless the error level is "0", the determination is "Yes." If the determination is "Yes," Step S28 ensues; if "No," later-described Step S29 ensues.

In Step S28, the processing unit 12 writes the determined error level to the user control database 14.

In Step S29, the processing unit 12 determines whether step S23 through Step S28 have been performed for all registered analyzers 2. If "Yes," operations return to Step S21, that is, it waits for the date to change. If "No," then operations return to Step S22, and chooses another analyzer as the subject user.

(2-3) QC Process

Figure 6:
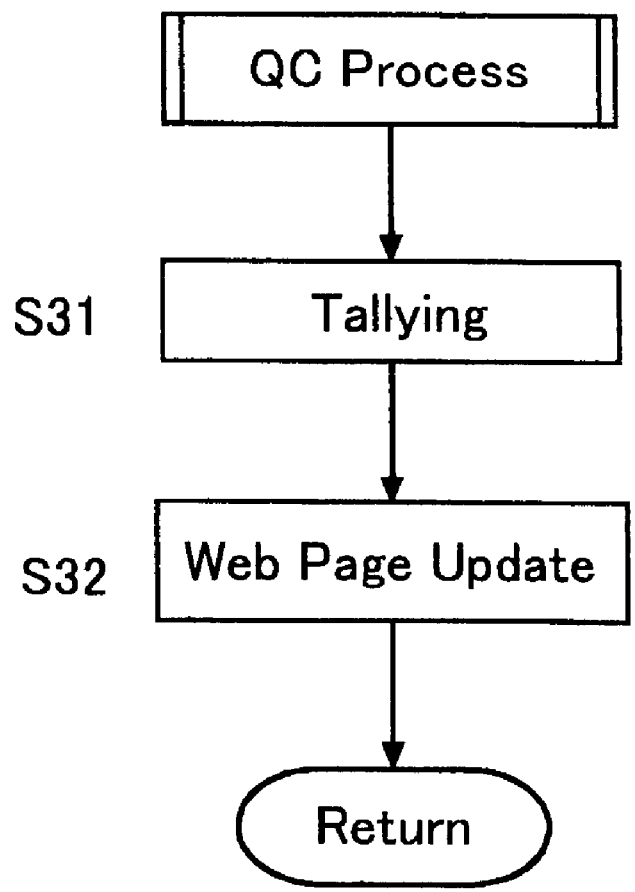
FIG. 6 is a flowchart showing one example of QC process flow performed by the control device.

FIG. 6 is a flowchart showing the flow of the QC process the control device 1 performs. In the above-discussed main process, when the control device 1 receives sample data from any analyzer 2, the control device 1 performs the following QC process. In other words, it tallies sample data including newly received sample data, and updates the Web page for each analyzer using the new tally results.

In Step S31, the processing unit 12 tallies sample data in which newly received sample data is included. Multiple varieties of quality control substances, such as those whose value is high and those whose is low, and those whose value is within normal range and those whose is within abnormal range, are often employed in same assay category. Wherein the quality control substance is from vital components, values from lot to lot—that is, the lot number for each manufacturing instance—will routinely differ. Furthermore, assaying mode under which the sample data was assayed must be taken into consideration in order to determine correction values for the assayed data. The control substance type, lot number, and assaying mode are reported from the analyzer to the control device in a manner to be described later.

Statistical tallying is conducted for each sort of analyzer and for each kind of quality control substance. Because substances like blood, which are liable to change (denature in the case of blood) over time, are used as the quality control substance, tallies are made per assay day to raise the reliability of the tally results. That the latest tally results are presented in real time in the present invention engenders the risk that the reliability of the tally results is not kept up at an early morning hour, with the total count of sample data for that day's assays being insufficient. Therein, the tally for that day's assays is made on sample data received, for example, within the past 24 hours. In this way, sample data from assaying conditions under the same elapsed-time changes can be employed, which prevents the total count from fluctuating markedly according to time slot. At the point the date changes, the tally results within the past 24 hours are set as the tally results for that day.

To improve the reliability of the tally results, it is preferable that cutoff values of mean plus or minus 3SD be used, and that values far outside the normal range not be included in the analysis. When the tally results are presented in the form of the average value of the sample data, and there is a very small amount of data for a 24-hour period, it would be better to use median value in place of average value.

In Step S32, the processing unit 12 updates the Web page for each analyzer based on the new tally results. Then it returns to the main process and severs the connection with the user terminal.

It should be noted that the timing for updating the tally results is not limited to being based on the time sample data was received, as long as the timing is such that the latest tally results can be presented to the analyzer. For example, one conceivable alternative would be to update the tally results when a Web page has been accessed from an analyzer. Or, the tally results may be updated at a predetermined time interval set in consideration of the load being placed on the analyzer.

(2-4) Other Processes

The control device 1 performs other processes in addition to main process, support process and QC process.

For example, the WWW server 16 provides a Web page when the WWW browser on the analyzer has accessed the Web page. On this occasion, it is preferable that the analyzer perform the authentication process in the form of an interface program, such as a library or CGI (Common Gateway Interface) scripts.

Also, the processing unit 12, in response to instructions from the operator of the control device 1, displays error log stored in the user control database 14.

(3) Analyzer Process Flow

Figure 7:
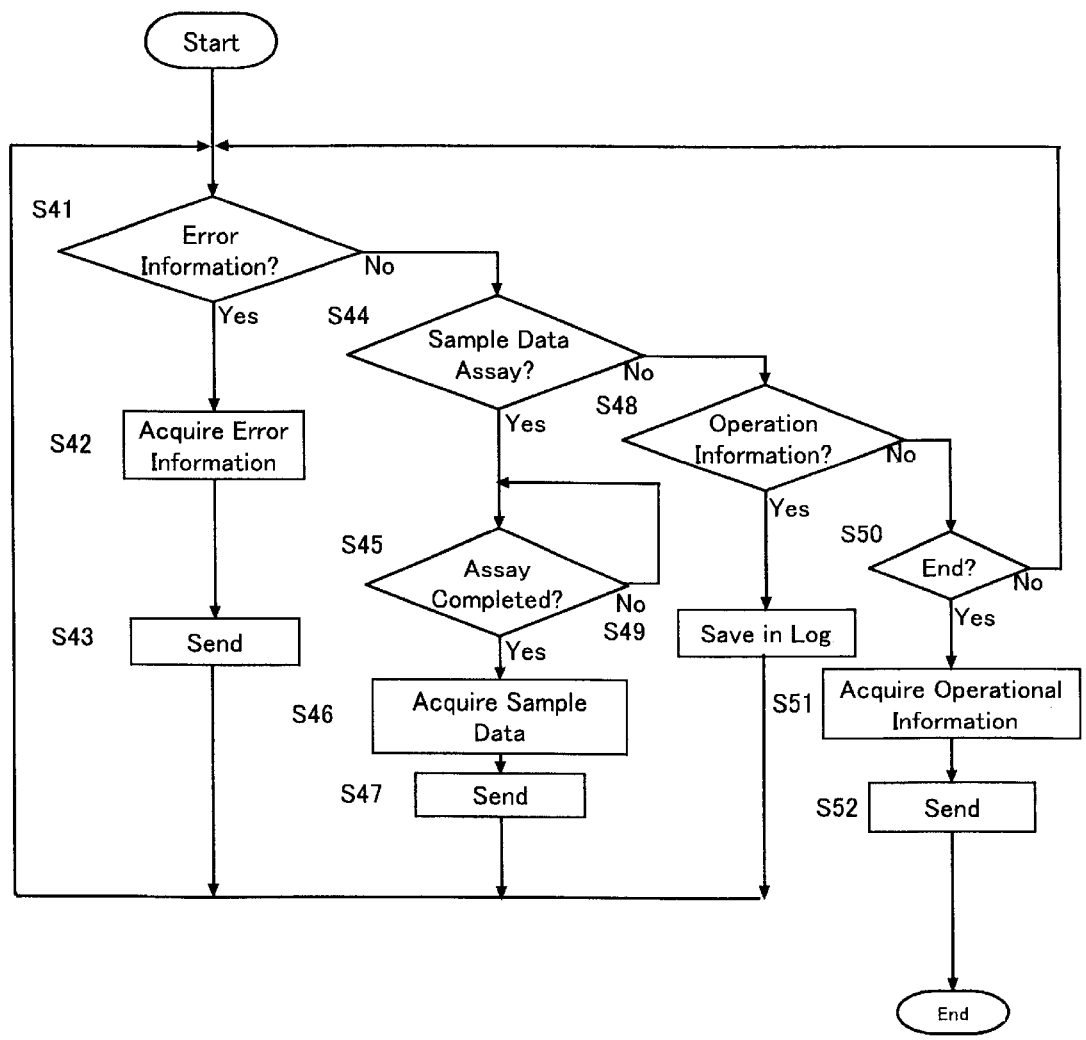
FIG. 7 is a flowchart showing one example of flow in a main process performed by an analyzer.

FIG. 7 is a flowchart showing one example of the flow of the main process performed by the analyzer. The analyzer 2 transmits error information and sample data in real time, and transmits operational information other than error information when the operations of the device end. FIG. 7 shows only the flow according to the present invention. When the analyzer is activated, the following process commences.

In Step 541, the control Unit 28 monitors the operational conditions of the analysis unit 21 and determines whether error information has occurred or not, if the determination is "Yes," then Step S42 ensues if "No," then Step S44, explained later, ensues.

In Step S42, the control unit 28 acquires error information from the analysis unit 21 and processes it to be data for email. For example, it creates email in which analyzer authentication information and error information is written into the main body of the text.

In Step S43, the control unit 28 activates the e-mail server 24 and transmits the created email. Then operations return to Step S41.

In Step S44, the control unit 28 determines whether sample data is to be collected. If the determination is "Yes," then Step S45 ensues. If "No," later-explained Step S48 ensues.

In Step S45, the control unit 28 stands by for termination of the assay. Upon completion Step S46 ensues.

In Step S46, the control unit 28 acquires sample data from the control device 1 and processes it to be data for email. For example, it writes authentication information into the text of the email, and creates an email with the sample dated attached as a file attachment. Other information needed when analyzing sample data may be included in the file attachment, for example, lot number, type of quality control substance, assay mode, and device ID. Device ID is identification information for the purpose of identifying an analyzer on this system, and is used to prevent sample data from being entered more than once during analysis.

In Step S47, the control unit 28 activates the e-mail server 24 and transmits the created email.

In Step S48, the control unit 28 awaits for operational information showing the operational conditions of the control device 1 other than error information. Operational information other than error information can include number of times operated, operation program, set-up conditions and the like. When operational information arises, operations proceed to Step S49. In all other cases, the process flow proceeds to Step S50.

In Step S49, the control unit 28 saves in a log the operational information that has arisen.

In Step S50, the control unit 28 determines whether instructions have been given for completion of the analyzer if the determination is "No," then the operations return to Step S41, if "Yes," then Step S51, described later, ensues.

In Step S51, the control unit 28 acquires operational information from the log and processes this to be email data. For example, it creates email in which analyzer authentication information and operational information are written into the text of an email.

In Step S52, the control unit 28 activates the e-mail server 24 and transmits the created email. After that, the control unit 28 terminates operations.

Figures 10, 11:
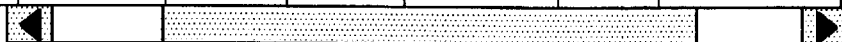
FIG. 10 is a program log display example.
FIG. 11 is an operation count display example.

Specific Example of Operational Information Stored in History Database by Support Process An explanation will be given in detail regarding the operational information stored in the user control database 14 by the support process described above. FIG. 8 through 11 show examples of operational information displayed at the control device 1 when a hemanalyzer has been used as the analyzer. FIG. 8 shows an example of an operational information selection screen, FIG. 9 shows an example of error log, FIG. 10 shows an example of program log, and FIG. 11 shows an example of number of times operated.

The operational information selection screen of FIG. 8 accepts selections for error log, program log, settings, or number of times operated. An operator can use this screen to designate analyzer and type of analyzer.

FIG. 9 shows an example of a screen displayed when "error log" has been selected on the operational information selection screen of FIG. 8. Error date and time, error message describing error, error code specifying error, and detailed code 1 and detailed code 2 are displayed. This error log displays, for example, the latest month worth of error log stored in the history database. It is preferable that it be possible to make settings for sort and filter for each field. It is also preferable that records of abnormalities that have a high possibility of being the cause of trouble be displayed in an easily distinguishable reverse display or the like. Record of abnormalities, for example, are records of the above-described error level being above a predetermined value.

FIG. 10 shows an example of a screen displayed when "program log" has been selected on the screen of FIG. 8. In this example, the program name of the program operated at the designated analyzer, the version thereof, and the time and date operated are displayed.

FIG. 11 shows an example of a screen displayed when "operation count" has been selected on the screen of FIG. 8. In this example, the number of times that a predetermined unit of the analyzer has been operated is displayed along with the operation date and time.

Although not shown in the figures, when "settings" is selected on the selection screen of FIG. 8, the setting terms for the analyzer are displayed.

Specific Example of Web Page Created by QC Process

An explanation will be given of a specific example of a Web page created by the control device 1 using the QC process described above. FIGS. 14 and 15 show examples of Web pages created by the processing unit 12. As before, these are examples of displays of tally results when analyses are made of a quality control substance using the hemanalyzer.

When a WWW browser on an analyzer accesses the control device 1, the window shown in the top half of FIG. 14 is displayed. This window allows the selection of a display style for the tally results. Here, an SDI chart has been selected as the "reporting style," causing the window shown in FIG. 15 to be displayed.

In FIG. 15, a predetermined graph is displayed for each blood component. This graph is created for each type of analyzer and each quality control substance. This graph is capable of displaying the past month's daily sample data for the accessing user and reference machine data. The reference machine data is sample data from assaying a predetermined quality control substance taken at an analyzer of the provider of the remote support system. The graph also displays degree of deviation from mean value, 1SD (1 standard deviation) by 1SD. The daily tally results are finalized when the date changes.

In terms of internal quality control, the as is display of these assay values allows confirmation of the fluctuations in sample data from an analyzer. In terms of external quality control, confirmation is possible of the fluctuations in the sample data from an analyzer against the overall average, using the overall average at the time of taking the sample data, as shown in FIG. 15. By changing the display as he sees fit, a user can make a visual comparison to see how much the sample data of the analyzer deviates from the overall average and the reference machine data. Furthermore, the Web pages on FIGS. 14 and 15 are updated immediately after sample data has been submitted. Therefore, a user can perform external quality control for the sample data he has submitted in real time, without a time lag.

Figure 16:
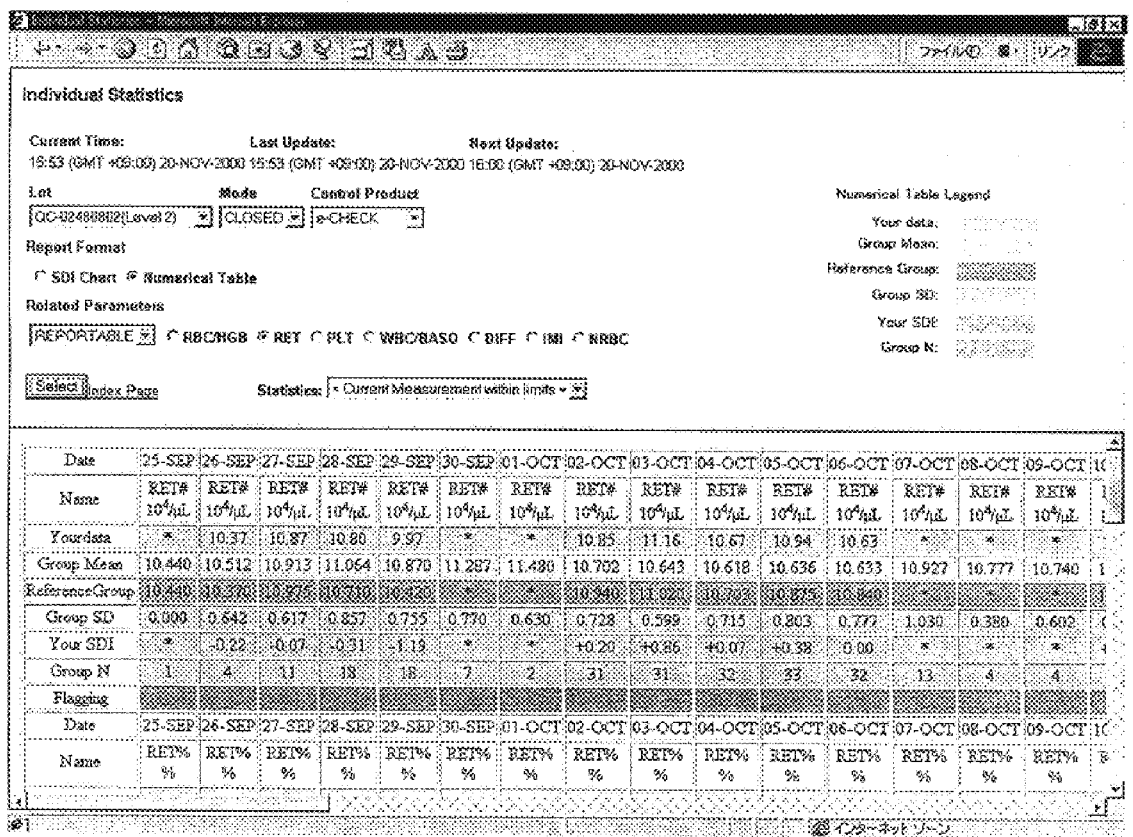

FIG. 16 is another display example of tally results for a quality control substance. In this example, the assay values for the user's analyzer, overall average value, and reference machine data are displayed individually. Because there are times when the user wants to make direct comparisons between the assay values of his own analyzer and the overall average and reference machine data, it is preferable to make it possible to display individually the values in FIG. 15 that are displayed within a chart.

Figure 17:
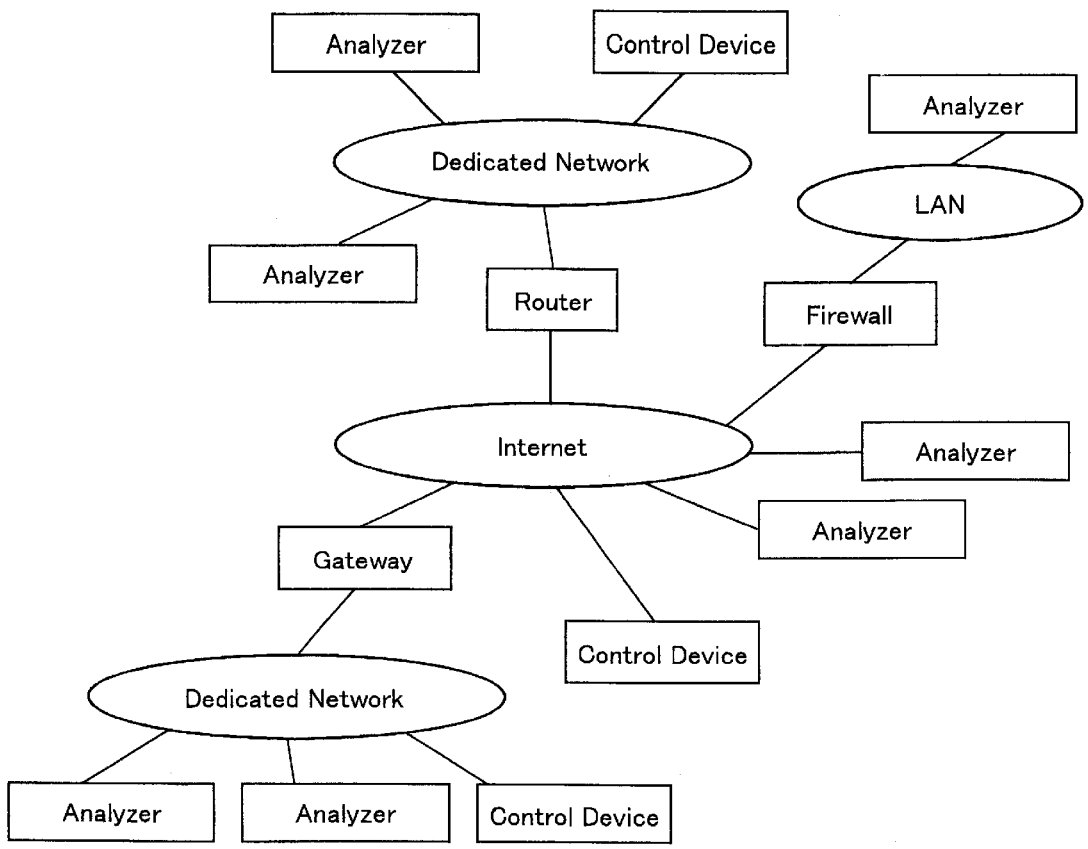
FIGS. 17 and 18 are overall configurational examples of a remote support system relating to another embodiment.
Figure 18:
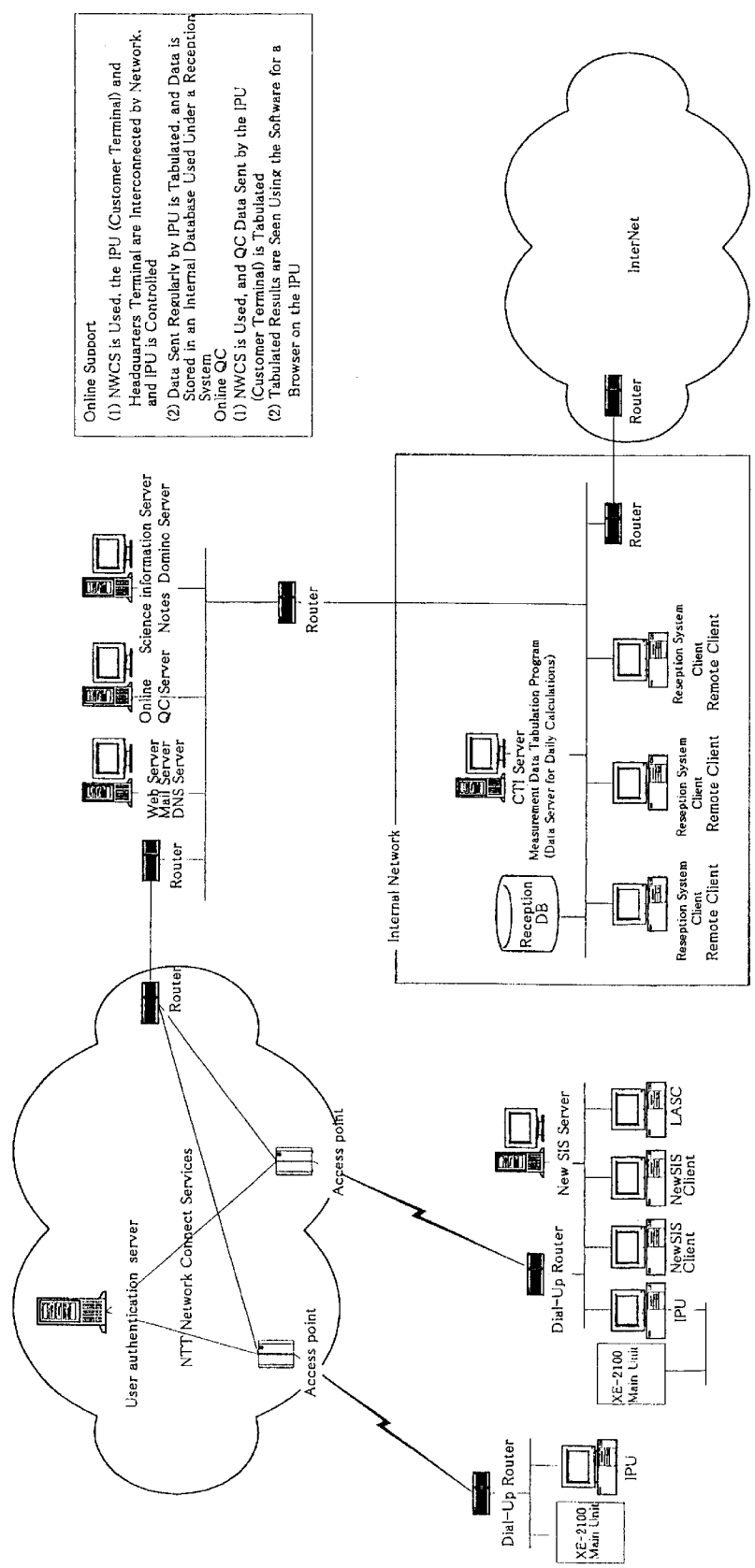

Other Embodiments (A) FIGS. 17 and 18 are block diagrams showing other examples of the remote support system. The network linking the user terminal and the analyzer does not necessarily have to be a dedicated network, but may be the Internet or a LAN. However, when the Internet is used, encoding and a stricter authentication system need to be used to heighten security when transmitting information.

It is not necessary for there to be just one control device on the system. For example, separate dedicated networks may be connected by the Internet and routers and gateways, and a control device may be provided for each dedicated network. In addition, a control device can collect predetermined information from analyzers of a dedicated network, for example analyzers on the Internet connected via a dedicated network and router, or analyzers connected to a LAN connected to the Internet via a firewall.

(B) In the above first embodiment, possible differences in times zones between the control device 1 and the analyzers 2, and among analyzers when the QC process is conducted are not taken into consideration. Therefore, as the second embodiment, an explanation will be given of the QC process in a remote support system having a control device and analyzers in different times zones.

(B-1) System Operation

Analysis of sample data is conducted in the following way. In the same manner as the first embodiment, data collected in the past 48 hours is tallied, and those results become real time tally results. Alternatively, the tally results for each day are computed by tallying from among the data collected in the past 48 hours, that data collected during the previous day.

To make it easy for operators of analyzers in each time zone to confirm tally results, tally results are correlated with those time zones (i.e., local time) and so inscribed.

However, when the reference time for analysis is set as local time, the reference time will differ from time zone to time zone, and thus analyses have to be conducted for each time zone. This means that there will be 24 different tally results across the world for a single date, making operation of the system complicated. On top of this, there are countries that have more than one time zone, and group hospitals that are located across more than one time zone.

On the other hand, when one of the time zones is the basis for the analysis reference time, without regard to local time, the differential between local time and reference time becomes a problem. For example, confusion will result if the date of the QC process changes in the middle of the analysis of an analyzer.

For this reason, to ensure that the tally results for a given day are the same for all time zones, the tally results for that day are computed with sample data having the same assay date (local time) according to each time zone.

(B-2) Base

In consideration of the above, in this embodiment, the reference time for the control device 1 is made to be the world's most advanced time, namely, GMT (Greenwich Mean Time)+12 hours. In the explanation below, the reference for time of day is the time of day of the time zone in which the control device 1 is located, in this instance, GMT+12 hours. Each analyzer 2 transmits to the control device 1, along with the sample data, the assay time and date in the time zone in which it is located. The control device 1 conducts analysis of the sample data based on sample data having an assay time and date within the past 48 hours. The reason for tallying sample data for the past 48 hours rather than the past 24 hours is to ensure that there will be a sufficient number of sample data sets N that will form the basis of the analyses.

FIG. 19 is a conceptual diagram of data transmitted from the analyzer 2 to the control device 1. Included in this data are lot number, type of quality control substance, assay mode, device ID, time zone, time of day, and sample data. Except for time zone and time of day, all other data is the same as in the first embodiment. For time zone, the time zone in which the analyzer 2 is located is given. For time of day, the assay date and time in the time zone in which each analyzer is located is given. The control device 1 conducts the QC process to be discussed later based on sample data having assay date and time within 48 hours of the time of day in the time zone in which the control device is located.

Figure 20A:
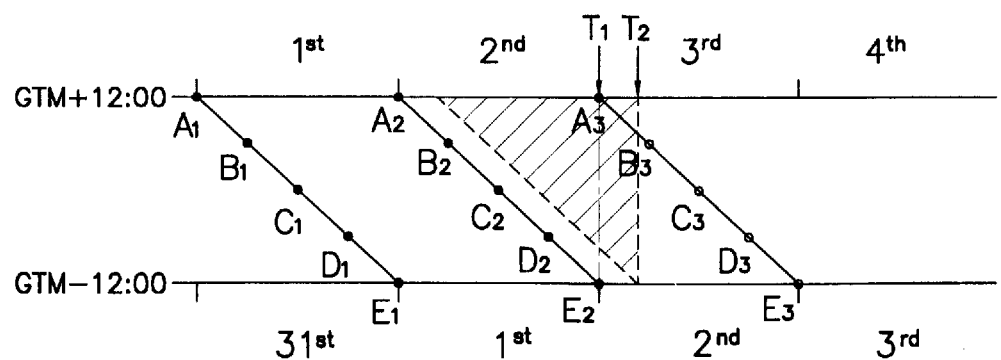
FIG. 20A is wherein the past 24 hours are the tallying object.

FIG. 20A is an explanatory diagram showing there being an insufficient number of sample data sets N received in the past 24 hours. To facilitate the explanation, let us suppose that analyzers A, B, C, D, and E, located in different times, transmit sample data daily at the time of 00:00. Analyzer A is in the GMT+12 hours time zone. Analyzer E is in the GMT−12 hours time zone, and analyzers B, C, and D are in time zones in between. The control device is in the GMT+12 hours time zone.

In FIG. 20, sample data with a date of X are indicated as $A_x$, $B_x$, etc. For example, $A_1$, $A_2$, and $A_3$ represent sample data from analyzer A dated the $1^{st}$, $2^{nd}$ and $3^{rd}$, respectively. Black circles represent sample data that has already been collected, and white circles represent sample data that has not yet been collected.

Figure 20B:
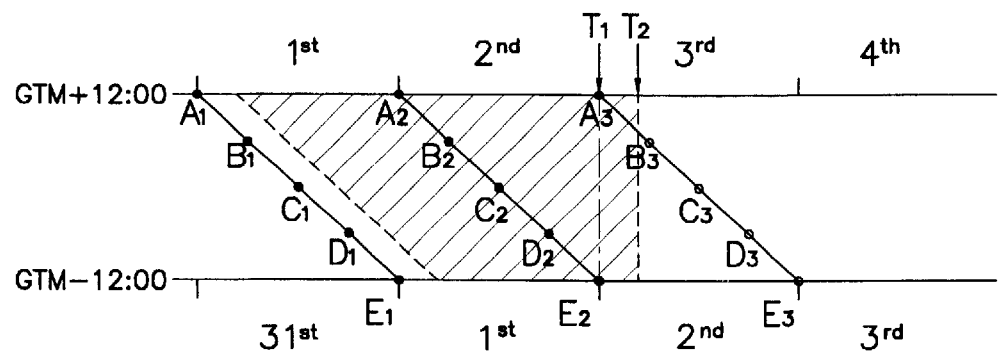
FIG. 20B is wherein the past 48 hours are the tallying object.

When the time for the control device is 00:00 on the $3^{rd}$ (time of day T1), $A_2$, $B_2$, $C_2$, $D_2$ and $E_2$ are included in the sample data from the past 24 hours. However, when a little time passes and the time of day becomes time of day T2, all that is included in the sample data from the past 24 hours is the data in the shaded triangular region in the figure, that is, only $A_3$. In such a case, the further a time zone is from GMT+12 hours, the greater the possibility that the sample data will not be tallied, meaning that there will be an insufficient number of data sets N and that it will be difficult to always provide reliable tally results FIG. 20B is an explanatory diagram showing there being a sufficient number of data sets N when the analysis is based on sample data received in the past 48 hours. When the time for the control devices reaches 00:00 on the $3^{rd}$ (time of day T1), sample data from analyzers A through E dated the $1^{st}$ and $2^{nd}$ ($A_1$, $B_1$, $C_1$, $D_1$, $E_1$; $A_2$, $B_2$, $C_2$, $D_2$, $E_2$) are included within the sample data from the past 48 hours. Next, when a little time passes and the time of day becomes time of day T2, the data within the shaded trapezoidal region in the figure (i.e., $A_2$, $B_2$, $C_2$, $D_2$, and $E_2$) becomes the population for analysis. In actuality, while the assay time differs for each analyzer, making the analysis population the sample data of the past 48 hours makes it possible to ensure that there is always a number of sample data sets close to the total number of analyzers on the system. If there is a plurality of sample data sets from the same analyzer within the population, all such sets other than the sample data set with the most recent assay time may be excluded from the analysis.

It should be noted that the reference time for the control device is not limited to GMT+12 hours. It is also possible to make the period of time subject to analysis longer than 48 hours or shorter than 48 hours; however, 48 hours is expedient in terms of system operations.

(B-3) Process Flow

With the exception of the QC process sub-routine (Step S8 in FIG. 4) performed after receipt of sample data, the process performed by the control device 1 relating to this embodiment is the same as with the first embodiment. A detailed explanation follows below of the QC process in this embodiment. The QC process of this embodiment is divided into (1) a current-day's tallying process and (2) the previous day's tallying process.

(B-3-1) Conceptual Illustration of a Current-Day's Tallying Process

Figure 21A:
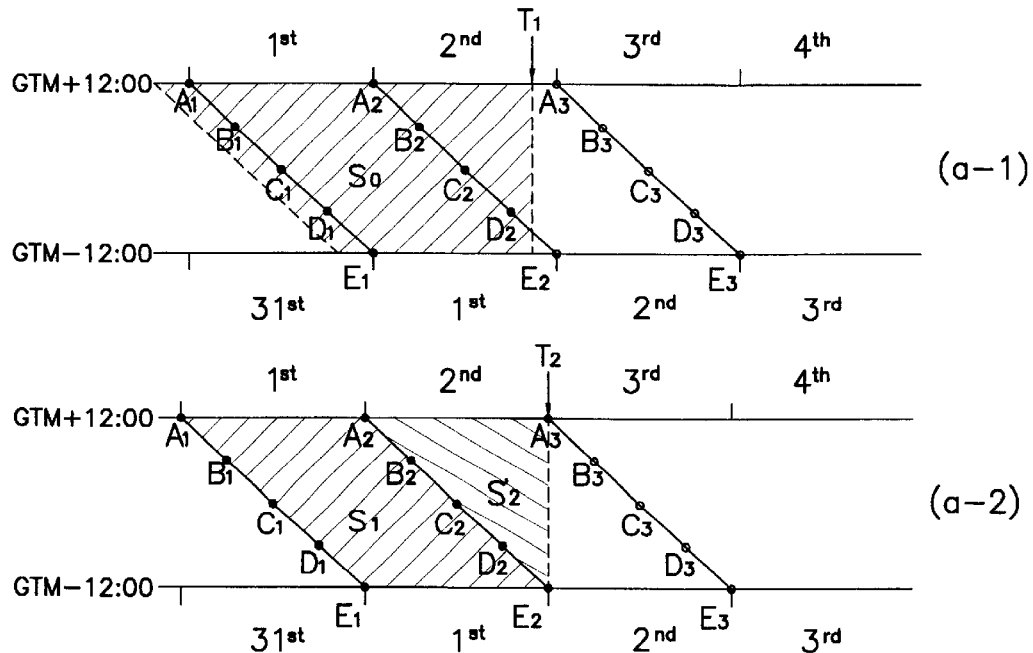
FIG. 21A is conceptual explanatory diagram of a current-day's tallying process.

FIG. 21A is a drawing explaining the concept of a current-day's tallying process. In the current-day's tallying process, first preliminary populations made up sample data dated within the past 48 hours are sequentially created, with the time of the control device 1 as reference. Furthermore, sample data analysis is conducted based on the first preliminary population, and the current-day's tally results are updated. In this embodiment, the update and tallying process of the first preliminary population is conducted every 10 minutes.

In FIG. 21($a$-1), the shaded trapezoidal region S0 shows the first preliminary population at the current time of day T1 (18:00 on the $2^{nd}$). With the passage of time the trapezoidal region S0 progresses to the right in the figure. That is, the first preliminary population is updated. As the first preliminary population is updated, the tally results for today (i.e., the $2^{nd}$) are also updated.

At the point of time T2 (00:00 on the $3^{rd}$) when the date changes from the $2^{nd}$ to the $3^{rd}$, the previous day's tallying process for finalizing the tally results of the second is activated. In FIG. 21A($a$-2), the shaded trapezoidal region, i.e., the sum of region S1 and S2', represents the first preliminary population at time of day T2. Region S1 represents the group of sample data sets dated the $1^{st}$ and region S2' represents the group of sample data sets dated the $2^{nd}$ that were obtained at this point in time.

Even if the previous day's tallying process has been activated, the current-day's tallying process continues to be conducted in the same manner as described above. The current-day's tallying process, as it continues, updates the tally results of today (i.e., the $3^{rd}$) according to a predetermined timing.

(B-3-2) Explanation of a Previous Day's Tallying Process

Figure 21B:
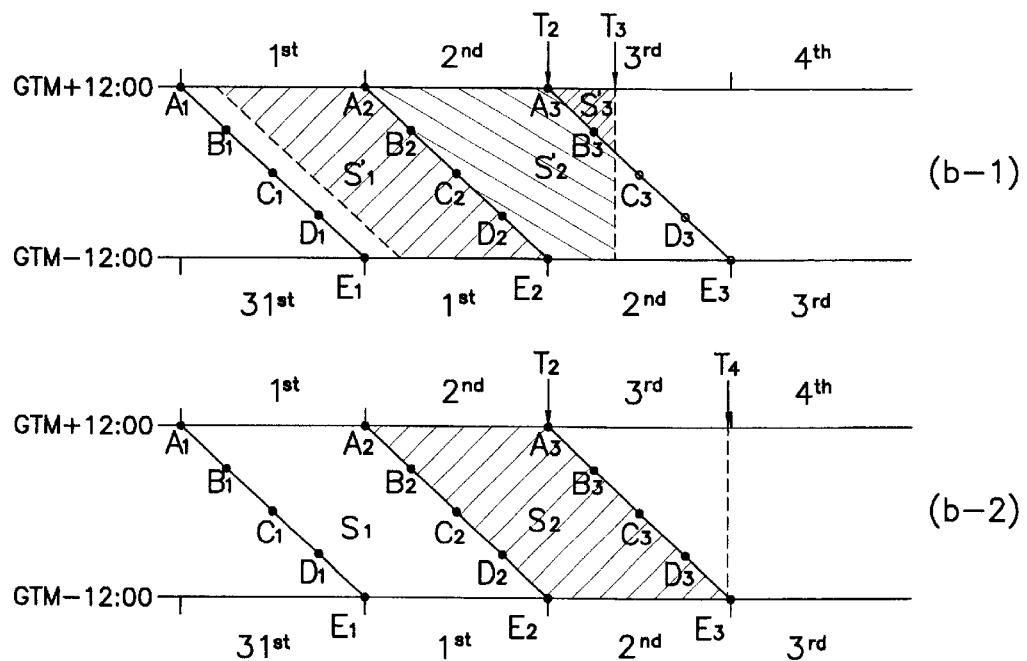
FIG. 21B is conceptual diagram of the previous day's tallying process.

FIG. 21B explains a previous day's tallying process. When this process has been activated at 00:00 on the $3^{rd}$, the control device 1 creates a second preliminary population. The control device 1 updates the second preliminary population every 10 minutes, and updates the tally results for the previous day (i.e., the $2^{nd}$) based on the updated second preliminary population.

The creation and update of the second preliminary population is conducted as follows. Every 10 minutes the control device 1 creates a second preliminary population made up of sample data from the past 48 hours. As the time of day progresses from T2 (00:00 on the $3^{rd}$), sample data dated today (i.e., the $3^{rd}$) that was collected in advanced time zones is deleted from the created second preliminary population.

FIG. 21($b$-1) shows a second preliminary population at time of day T3 (10:00 on the $3^{rd}$), 10 hours after time of day T2. Region S1' is that group of sample data dated the $1^{st}$ having an assay time within 48 hours of T3. Region S2' is a group of sample data with an assay date of the $2^{nd}$ that has already been collected. Region S3' is that sample data from the past 48 hours that is dated the $3^{rd}$ and is to be deleted from the second preliminary population. At time of day T3, the control device computes the tally results for the previous day (the $2^{nd}$) based on the sample data from region S1' and region S2'.

FIG. 21($b$-2) is the second preliminary population at the point in time of time of day T4 (00:00 on the $4^{th}$), which is 24 hours after time of day T2. The shaded region S2 indicates the second preliminary population at this point in time. The second preliminary population at this point in time comprises the group of sample data sets dated the $2^{nd}$ from all the analyzers participating in the remote support system. At this point in time, the control device 1 finalizes the population for the analysis of the day two days prior (the $2^{nd}$). The tally results obtained from this population become the final tally results for the day two days prior (the $2^{nd}$).

(B-4) Flowchart

In this embodiment, the control device I conducts three types of QC process independently: a collection process, the current-day's tallying process, and the previous day's tallying process.

(B-4-1) Collection Process

Figure 22:
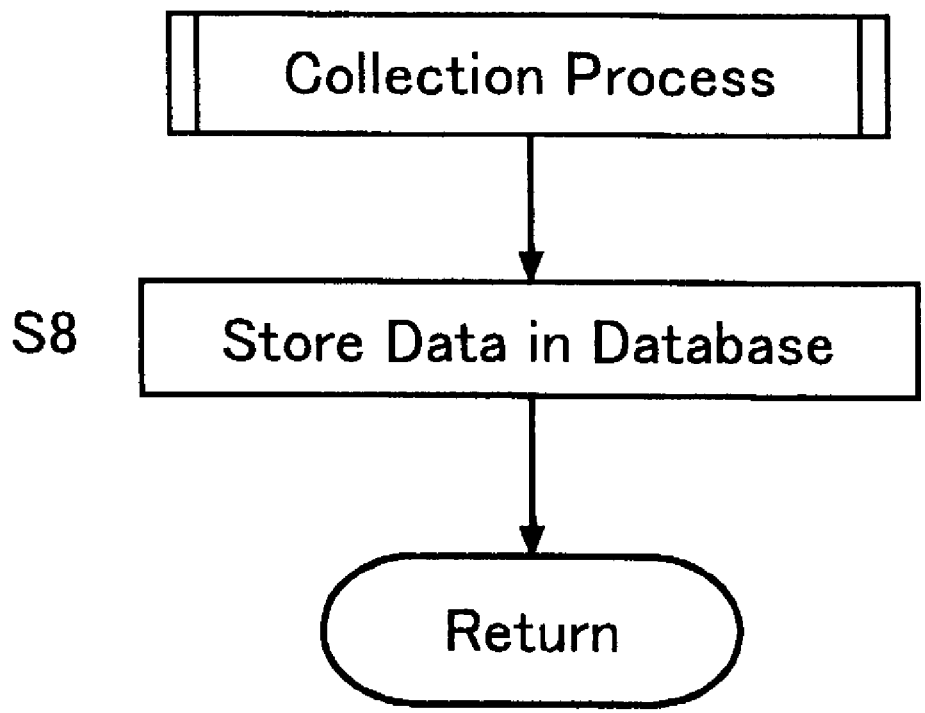
FIG. 22 is flowchart showing one example of flow in a collection process.

FIG. 22 is a sample data collection process that the control device 1 performs. This process commences when Step S8 (QC process sub-routine) ensues in the main process executed by the control device 1 (FIG. 4). In other words, in this embodiment, each time the control device 1 receives sample data, that data is stored in the base database (not shown in figure). The sample data that the control device 1 receives is stored in this base database without any deletions.

(B-4-2) A Current-Day's Tallying Process

Figure 23:
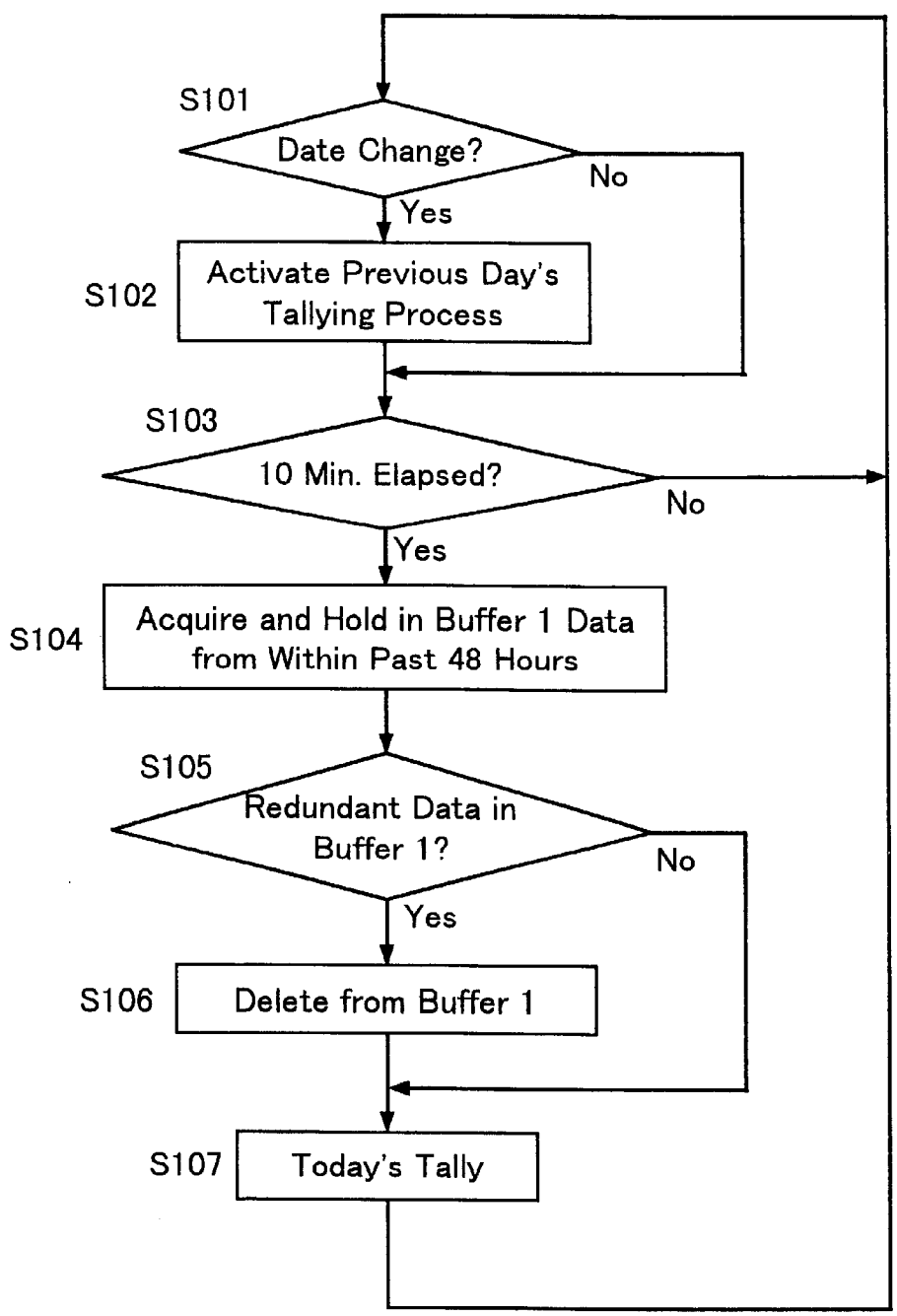
FIG. 23 is flowchart showing one example of flow in a current-day's tallying process.

FIG. 23 is a flowchart showing the flow of the current-day's tallying process performed by the control device 1. In the explanation below, a buffer 1 shall be the work area for forming the first preliminary population that will serve as the basis for the current-day's tallying process.

Steps S101, S102: The control device 1 determines whether the date has changed (S101). If it has changed, it activates the previous day's process (S102) (refer to FIG. 21(a-2).

Steps S103, S104, S105, S106: The control device 1 determines whether a predetermined time, i.e., 10 minutes, has elapsed since the previous analysis (S103). If it hasn't elapsed, operations return to Step S101 without analyses being made. If it has elapsed, the first preliminary population is updated and the current-day's analysis is updated.

Specifically, sample data having a time and date within the past 48 hours is first acquired from the base database and is held in the buffer 1 (S104). Next, it is determined whether among the data held in the buffer 1 there is more than one set of data from the same analyzer (S105). If there is, all such data except the most recent is excluded from the buffer 1 (S106) [refer to FIG. 21(a-1)].

Step S107: The control device 1 performs analyses based upon the updated first preliminary population. These tally results will serve as the current-day's tally results for this point in time.

The control device 1 performs the above process independently of the sample data collection process, and updates the current-day's tally results every 10 minutes, based on sample data from within the past 48 hours.

(B-4-2) A Previous Day's Tallying Process

Figure 24:
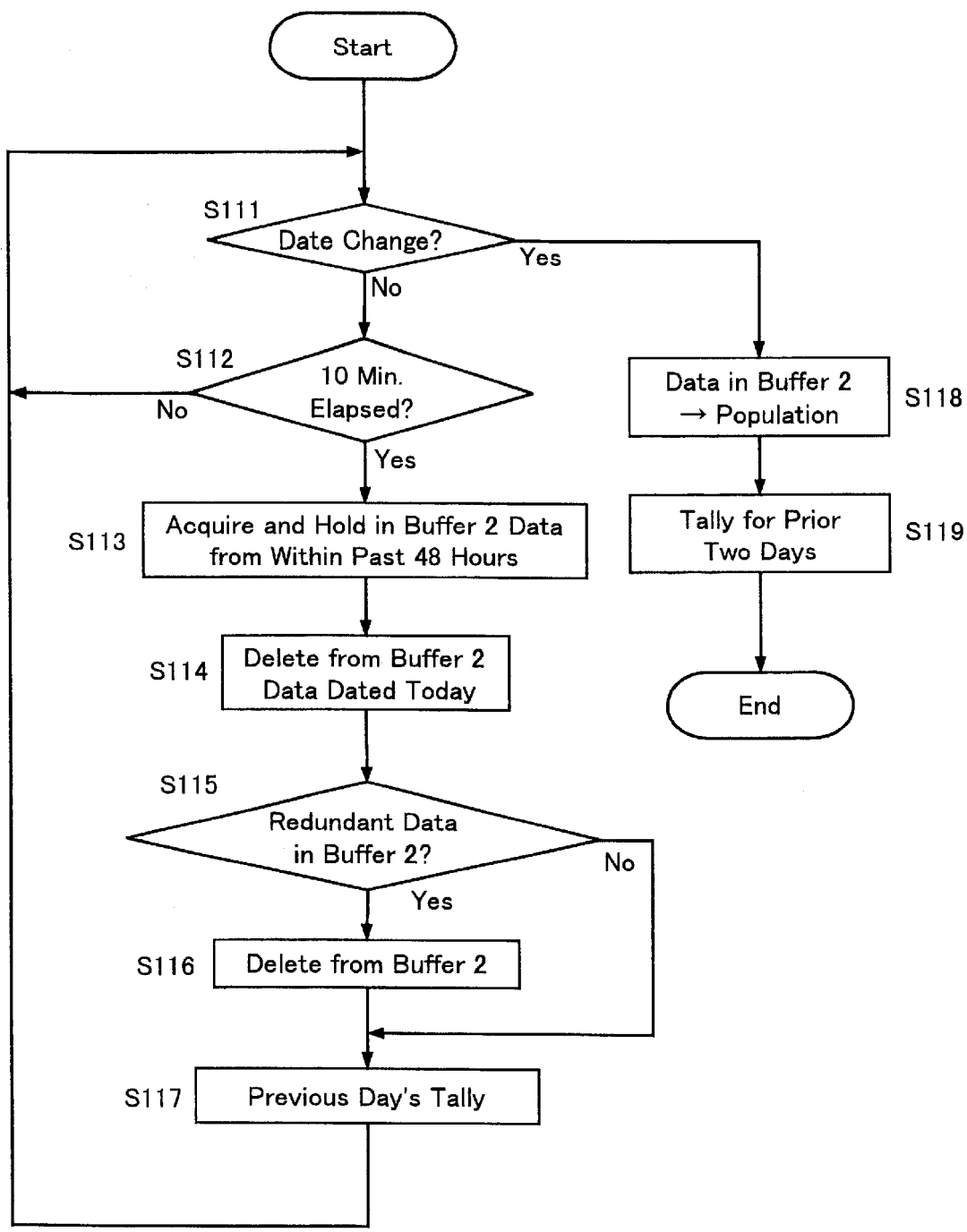
FIG. 24 is flowchart showing one example of flow in the previous day's tallying process.

FIG. 24 is a flowchart showing the flow of the previous day's tallying process that the control device 1 performs. In the explanation below, a buffer 2 shall be the work area for forming the second preliminary population that will serve as the basis for the previous day's tallying process. When operations in the above-described the current-day's tallying process proceeds to Step S102, the following process is activated. As with FIG. 21 above, we will suppose that this process commenced at time of day T2 (00:00 on the $3^{rd}$).

Step S111: The control device 1 again determines whether the date has changed; if it hasn't the process starting with Step S112 is performed. In other words, until the time of day changes from T3 (00:00 on the $3^{rd}$) to T4 (00:00 on the $4^{th}$), the update of the second preliminary population and update of the analysis are conducted (S112 to S117, described below). When the time of day reaches 00:00 on the $4^{th}$, the tally results of two days prior, that is, the $2^{nd}$, are finalized (Steps 118 through 120 described below).

Step S112: The control device 1 determines whether 10 minutes have elapsed since the previous analysis. If the determination is "Yes," then Step S113 ensues, and the second preliminary population is updated. If the determination is "No," it does not update the preliminary population and operations return to Step S111.

Steps S113, S114, S115, S116: The control device 1 acquires from the base database sample data from within the past 48 hours and holds these in the buffer 2 (S113). Next, the control device 1 deletes data dated today (i.e., the $3^{rd}$) from the acquired sample data (S114). Next, it is determined whether among the data held in the buffer 2 there is more than one set of data from the same analyzer (S115). If there is, all such data except the most recent is excluded from the buffer 1 (S116). In this manner, the second preliminary population is updated [refer to FIG. 21(b-1)].

Step S117: The control device 1, based on the updated second preliminary population, newly computes tally results for the previous day, namely, the $2^{nd}$. In this manner the tally results for the $2^{nd}$ (the previous day) are updated every 10 minutes (S112 to S117).

Step S118: If it is determined at Step S111 that the date has changed, in other words, that the time of day has become 00:00 on the $4^{th}$, the control device 1 finalizes the population that will serve as the basis for the tally results of the $2^{nd}$. In other words, the second preliminary population at this point in time becomes the population for the tally results of two days prior (i.e., the $2^{nd}$) Only sample data dated the $2^{nd}$ is contained in the finalized population [refer to FIG. 21(b-2)].

Step S119: The control device 1 computes the tally results for two days prior based on the finalized population.

The display of the Web page on which the above tally results are posted is executed based on authentication information input from the analyzer. When a Web page is displayed, the control device 1 confirms the time zone of the analyzer. The reason for this is that it is conceivable that the local time in that time zone is a date other the date in the GMT+12 hours times zone, that is, it is not that date yet. In such cases, the control device I does not display the current-day's tally results for the GMT+12 hours time zone, but displays only the tally results of the previous day's tallying process.

With the above-described process, based on sample data collected from analyzers located across the world, the current-day's tallying process sequentially updates the current-day's tally results and the previous day's process updates the previous day's tally results. In addition, the tally results for each day are finalized through the previous day's tallying process. Because the analysis is performed based on there being at least a certain number of sample data sets, the reliability of the tally results can be improved. Furthermore, because sample data taken from assays in each time zone is reflected in that day's tally results, a user can use this system without being aware of any differences in time zones.

(C) Storage media on which is recorded the above-described programs of the present invention are included in the present invention. These media can include, among others, computer-readable floppy diskettes, hard disks, semiconductor memory, CD-ROMs, DVDs, and opto-magnetic disks.

(D) Media that transmit the programs of the present invention are also included in the present invention. These transmission media include telecommunication media (optical fibers, wireless networks, inter alia) in computer network systems (LAN, Internet, wireless communication network) for transporting and supplying program information as carrier.

Through the use of the present invention, the history of an analyzer is stored in a control device, thus making possible rapid response to trouble arising in the analyzer and shortening the down time of the analyzer. Also, the external control of an analyzer can be performed essentially in real time.

While only selected embodiments have been chosen to illustrate the present invention, to those skilled in the art it will be apparent from this disclosure that various changes and modifications can be made herein without departing from the scope of the invention as defined in the appended claims. Furthermore, the foregoing description of the embodiments according to the present invention is provided for illustration only, and not for the purpose of limiting the invention as defined by the appended claims and their equivalents.

What is claimed is:

1. A support method for analyzers adapted to be employed in a control device connected to a plurality of analyzers via a network, the support method comprising computer-implemented steps of:
   collecting from each of the analyzers via the network operational information of the analyzer when the analyzer shuts down;
   storing the collected operational information for each analyzer; and
   outputting the collected operational information in response to an instruction by an operator of the control device.

2. An analyzer connected to a control device via a network, the analyzer comprising:
   analyzing means for analyzing substance to be analyzed;
   operational information generation means for generating operational information of said analyzer based on an operational status of said analyzing means; and
   transmission means for transmitting at least some of the operational information to the control device via the network when said analyzing means shuts down.

3. The support method for analyzers as set forth in claim 1, further comprising a computer-implemented step of
   classifying the operational information that is collected from the analyzers according to type of the operational information.

4. The support method for analyzers as set forth in claim 1, further comprising a computer-implemented step of
   collecting quality control sample data from each of the analyzers as the analyzer determines that the sample that is analyzed is quality control sample and generates the quality control sample data.

5. The support method for analyzers as set forth in claim 4, further comprising computer-implemented steps of
   detecting a trouble in an analyzer based on the quality control sample data collected from the analyzers; and
   notifying the analyzer of the trouble.

6. The support method for analyzers as set forth in claim 5, further comprising a computer-implemented step of
   remotely accessing and operating the analyzer in which the trouble was detected.

7. The support method for analyzers as set forth in claim 1, further comprising computer-implemented steps of
   receiving error information from an analyzer as the analyzer generates the error information; and
   remotely accessing and operating the analyzer which sent the error information.

8. The support method for analyzers as set forth in claim 1, further comprising computer-implemented steps of
   detecting a trouble in an analyzer based on the operation information collected from the analyzer; and
   remotely accessing and operating the analyzer in which the trouble was detected.

9. A support method for analyzers adapted to be employed in a control device connected to a plurality of analyzers via a network, the support method comprising computer-implemented steps of:
   activating a remote control unit of the control device such that the remote control unit of the control device is linked with a remote control unit of the analyzer; and
   remotely logging on to the analyzer such that a window displayed at the analyzer is at least partially displayed at the control device.

10. The support method for analyzers as set forth in claim 9, further comprising a computer-implemented step of
    operating the analyzer in response to an instruction inputted to the control device.

11. The support method for analyzers as set forth in claim 9, further comprising a computer-implemented step of
    preventing display of patient information at the control device if the window of the analyzer displays patient information.

12. A support method for analyzers adapted to be employed in a control device connected to a plurality of analyzers via a network, the support method comprising computer-implemented steps of:
    collecting quality control sample data from each of the analyzers in real time as the analyzer generates the quality control sample data from a quality control sample;
    tallying the quality control sample data for each quality control sample; and
    notifying the tally results to each of the analyzers.

13. The support method for analyzers as set forth in claim 12, wherein
    the quality control sample data is collected from the analyzer as the analyzer determines that the sample is a quality control sample and generates the quality control sample data.

14. The support method for analyzers as set forth in claim 12, further comprising computer-implemented steps of
    detecting a trouble in an analyzer based on the quality control sample collected from the analyzers; and
    notifying the analyzer of the trouble.

15. The analyzer as set forth in claim 2, further comprising
    classifying means for classifying the operational information into either of first operational information, which is urgent information, and second operational information, which is less urgent information; and
    said transmission means transmitting the first operational information to the control device via the network in real time as said classifying means classifies the operational information into the first operational information.

16. The analyzer as set forth in claim 15, wherein
    said transmission means transmitting the second operational information to the control device when said analyzing means shuts down.

17. The analyzer as set forth in claim 2, further comprising
    determination means for determining whether the substance to be analyzed is quality control sample,
    said transmission means transmitting quality control sample data in real time as said analyzing means generates the quality control sample data, where said determination means determines that the substance to be analyzed is quality control sample.

18. The analyzer as set forth in claim 17, further comprising
retrieval means for retrieving a result of tally that the control device performed based on the quality control sample data transmitted by said transmission means.

19. The analyzer as set forth in claim 18, further comprising
remote control means through which the control device operates said analyzing means remotely.

20. The analyzer as set forth in claim 2, wherein
the operational information includes error information.

21. The analyzer as set forth in claim 2, wherein
the operational information includes a number of times said analyzing means analyzed samples.

22. An analyzer connected to a control device via a network, said analyzer comprising:
analyzing means for analyzing substance to be analyzed;
operational information generation means for generating operational information; and
transmission means for transmitting at least some of the operational information to the control device via the network in real time as said operational information generation means generates the operational information.

23. The analyzer as set forth in claim 22, further comprising
classifying means for classifying the operational information into either of first operational information, which is urgent information, and second operational information, which is less urgent information; and
said transmission means transmitting the first operational information to the control device via the network in real time as said classifying means classifies the operational information into first operational information.

24. An analyzer connected to a control device via a network, the analyzer comprising:
analyzing means for analyzing substance to be analyzed;
determination means for determining whether the substance to be analyzed is quality control sample; and
transmission means for transmitting quality control sample data in real time as said analyzing means generates the quality control sample data, where said determination means determines that the substance to be analyzed is quality control sample.

25. The analyzer as set forth in claim 24, further comprising
retrieval means for retrieving a result of tally that the control device performed based on the quality control sample data transmitted by said transmission means.

26. A network-based analyzer support system, comprising:
a plurality of analyzers, each having
analyzing means for analyzing substance to be analyzed,
operational information generation means for generating operational information of said analyzer based on an operational status of said analyzing means, and
transmission means for transmitting the operational information to the control device via the network when said analyzing means shuts down; and
a control device connected to said plurality of analyzers via a network, said control device having
collection means for collecting the operational information from said plurality of analyzers, and
memory means for storing the collected operational information,
output means for outputting the operational information of a desired analyzer in response to an instruction by an operator of the control device.

27. The network-based analyzer support system as set forth in claim 26, wherein
at least one of said plurality of analyzers further comprising:
determination means for determining whether the substance to be analyzed is quality control sample,
said transmission means transmitting quality control sample data in real time as said analyzing means generates the quality control sample data, where said determination means determines that the substance to be analyzed is quality control sample.

28. The network-based analyzer support system as set forth in claim 26, wherein
at least one of said plurality of analyzers has remote control means, and
said control device has remote control means for operating said analyzer remotely through said remote control means of said analyzer.

* * * * *